US010167504B2

(12) United States Patent
Kotsbak

(10) Patent No.: US 10,167,504 B2
(45) Date of Patent: Jan. 1, 2019

(54) METHOD OF SEQUENCING

(75) Inventor: Jarle Kotsbak, Trondheim (NO)

(73) Assignee: GENESEQUE AS, Trondheim (NO)

( * ) Notice: Subject to any disclaimer, the term of this patent is extended or adjusted under 35 U.S.C. 154(b) by 503 days.

(21) Appl. No.: 13/876,176

(22) PCT Filed: Sep. 30, 2011

(86) PCT No.: PCT/EP2011/067201
§ 371 (c)(1),
(2), (4) Date: Oct. 22, 2013

(87) PCT Pub. No.: WO2012/042053
PCT Pub. Date: Apr. 5, 2012

(65) Prior Publication Data
US 2014/0045703 A1 Feb. 13, 2014

(30) Foreign Application Priority Data
Sep. 30, 2010 (GB) .................. 1016484.6

(51) Int. Cl.
C12Q 1/68 (2018.01)
C12Q 1/6874 (2018.01)

(52) U.S. Cl.
CPC .................. C12Q 1/6874 (2013.01)

(58) Field of Classification Search
CPC ........................................... C12Q 1/68
USPC ............................... 435/6.12, 91.2
See application file for complete search history.

(56) References Cited

U.S. PATENT DOCUMENTS

| 5,552,278 | A | 9/1996 | Brenner |
| 5,599,675 | A | 2/1997 | Brenner |
| 5,714,330 | A | 2/1998 | Brenner et al. |
| 5,750,341 | A | 5/1998 | Macevicz |
| 5,843,651 | A | 12/1998 | Stimpson et al. |
| 6,210,891 | B1 | 4/2001 | Nyren et al. |
| 7,323,305 | B2 | 1/2008 | Leamon et al. |
| 2002/0168663 | A1 | 11/2002 | Phan et al. |
| 2003/0215825 | A1 | 11/2003 | Tong |
| 2003/0215844 | A1 | 11/2003 | Chapsky et al. |
| 2004/0185466 | A1 | 9/2004 | Ju et al. |
| 2005/0059030 | A1 | 3/2005 | Bao et al. |
| 2005/0087000 | A1 | 4/2005 | Coehoorn et al. |
| 2005/0170367 | A1 | 8/2005 | Quake et al. |
| 2005/0244863 | A1 | 11/2005 | Mir |
| 2005/0250094 | A1 | 11/2005 | Storhoff et al. |
| 2006/0084069 | A1 | 4/2006 | Chan et al. |
| 2006/0127942 | A1 | 6/2006 | Straume et al. |
| 2008/0182235 | A1 | 7/2008 | Hearn et al. |
| 2008/0207464 | A1 | 8/2008 | Prins et al. |
| 2008/0311561 | A1 | 12/2008 | Ahn et al. |
| 2009/0036323 | A1 | 2/2009 | van Eijk et al. |
| 2009/0048124 | A1 | 2/2009 | Leamon et al. |
| 2009/0062129 | A1 | 3/2009 | McKernan et al. |
| 2009/0181853 | A1* | 7/2009 | Peter .................. C12Q 1/6837 506/9 |
| 2010/0009354 | A1 | 1/2010 | Nagai et al. |
| 2010/0035252 | A1 | 2/2010 | Rothberg et al. |
| 2010/0120132 | A1 | 5/2010 | Koo |
| 2010/0323355 | A1 | 12/2010 | Dittmer |
| 2011/0008775 | A1 | 1/2011 | Gao et al. |
| 2011/0171749 | A1 | 7/2011 | Alocilja et al. |

FOREIGN PATENT DOCUMENTS

| CN | 101245390 | 8/2008 |
| EP | 0 330 185 | 8/1989 |
| EP | 0 703 991 | 5/2001 |
| EP | 1 619 259 | 1/2006 |
| WO | 00/15844 | 3/2000 |
| WO | 02/079519 | 10/2002 |
| WO | 2004/007773 | 1/2004 |
| WO | 2004/094664 | 11/2004 |
| WO | 2007/092941 | 8/2007 |
| WO | 2009/024781 | 2/2009 |
| WO | 2010/016937 | 2/2010 |
| WO | 2010/109159 | 9/2010 |
| WO | 2012/042052 | 4/2012 |

OTHER PUBLICATIONS

International Search Report for PCT/EP2011/067201, dated Dec. 15, 2011.
Fuller, C. et al., The challenges of sequencing by synthesis, Nature Biotechnology, 2009, vol. 27, No. 11, pp. 1013-1023.
Shlyapnikov, Y. et al., Detection of microarray-hybridized oligonucleotides with magnetic beads, Analytical Biochemistry, 2010, vol. 399, No. 1, pp. 125-131.
Lehmann, U. et al., Microparticle photometry in a CMOS microsystem combining magnetic actuation and in situ optical detection, Sensors and Actuators B, 2008, vol. 132, No. 2, pp. 411-417.
Aksyonov et al., "Multiplexed DNA sequencing-by-synthesis", Analytical Biochemistry, 348:127-138 (2006).
Aytur et al., "A novel magnetic bead bioassay platform using a microchip-based sensor for infectious disease diagnosis", Journal of Immunological Methods, 314:21-29 (2006).
Braslavsky et al., "Sequence information can be obtained from single DNA molecules", PNAS, 100(7):3960-3964 (2003).
Edelstein et al., "The BARC biosensor applied to the detection of biological warfare agents", Biosensors & Bioelectronics, 14:805-813 (2000).
Guo et al., "Four-color DNA sequencing with 3'-O-modified nucleotide reversible terminators and chemically cleavable fluorescent dideoxynucleotides", PNAS, 105(27):9145-9150 (2008).
Gunderson et al., "Mutation Detection by Ligation to Complete n-mer DNA Arrays", Genome Research, 8:1142-1153 (1998).
Ju et al., "Four-color DNA sequencing by synthesis using cleavable fluorescent nucleotide reversible terminators", PNAS, 103(52):19635-19640 (2006).

(Continued)

Primary Examiner — Aaron A Priest
(74) Attorney, Agent, or Firm — Wenderoth, Lind & Ponack, L.L.P.

(57) ABSTRACT

The present invention provides a method of sequencing a polynucleotide using a stepwise ligation and cleavage method in which two or more cleavage enzymes which are specific to two or more test probes are used sequentially to identify which test probe bound and hence the sequence of the target polynucleotide. In a preferred aspect the probes and/or bases used in the reaction are labelled, e.g. with a bead.

23 Claims, 7 Drawing Sheets

Specification includes a Sequence Listing.

(56) References Cited

OTHER PUBLICATIONS

Maxam et al., "A new method for sequencing DNA", Proc. Natl. Acad. Sci. USA, 74(2):560-564 (1977).
Mir et al., "Sequencing by Cyclic Ligation and Cleavage (CycLiC) directly on a microarray captured template", Nucleic Acids Research, 37(1)e5:1-8.
Mulvaney et al., "Attomolar protein detection in complex sample matrices with semi-homogeneous fluidic force discrimination assays", Biosensors and Bioelectronics, 24:1109-1115 (2009).
Mulvaney et al., "Rapid, femtomolar bioassays in complex matrices combining microfluidics and magnetoelectronics", Biosensors and Bioelectronics, 23(2):191-200 (2007).
Ronaghi et al., "DNA Sequencing: A Sequencing Method Based on Real-Time Pyrophosphate", Science, 281(5375):363-365 (1998).
Sanger et al., "DNA sequencing with chain-terminating inhibitors", Proc. Natl. Acad. Sci. USA, 74(12):5463-5467 (1977).
Strick et al., "Behavior of Supercoiled DNA", Biophysical Journal, 74:2016-2028 (1998).
Wang et al., "Flexible Microarray Construction and Fast DNA Hybridization Conducted on a Microfluidic Chip for Greenhouse Plant Fungal Pathogen Detection", Journal of Agricultural and Food Chemistry, 55:10509-10516 (2007).

\* cited by examiner

METHOD OF SEQUENCING

The present invention concerns new stepwise ligation and cleavage methods of sequencing polynucleotides in which multiple different cleavage enzymes are used in the cleavage step(s), wherein the different enzymes are specific to different probes which bind to different bases within the polynucleotides. This allows the base or bases to be determined in the sequence based on the enzyme which effects cleavage.

Polynucleotide sequencing has been carried out by various methods for many years and has provided a mine of information concerning the genomes of different species. Even though the human genome has been sequenced, there is a great interest in resequencing in order to identify genetic predispositions or genetic or gene related diseases. Hence, the mapping of mutations and tissue specific mRNA production and expression analysis is of great interest. Additionally, the sequencing of genomes from other species is of interest i.e. de novo sequencing.

DNA sequencing has been traditionally carried out by the Sanger dideoxy method (Sanger, Nicklen and Coulson, Proc. Natl. Acad. Sci. USA, 1977, 74, 5463-7) which has been used since the 1980s. It is a multimolecular method based on electrophoretic filtering of cloned DNA that is firstly treated enzymatically. The enzymatic process produces single stranded DNA by interrupted polymerisation using a mixture of fluorophore labelled dideoxy NTPs which terminate chain extension and dNTPs which do not. Hence, a mixture of chain lengths is obtained using this process where the length of each DNA strand represents the base position and the colour of the connected fluorophore represents the identity of the base at the 3' end. These identities are read as aligned coloured dots, with one line of dots representing one DNA sequence. However, the Sanger sequencing method requires the use of multiple chains and sequencing is possible of only about 1000 bases.

The chemical degradation method of Maxam et al (Proc. Natl. Acad. Sci., 1977, 74, 560-4) has also been used for DNA sequencing and involves the cleavage of a nucleotide sequence at specific nucleotides, resulting in the production of chains of different lengths where each length is indicative of the presence of a particular nucleotide at that position. Thus the chemical degradation method also requires electrophoretic separation of strands for sequence determination.

Both the chain termination method of Sanger and the chemical degradation method of Maxam therefore require the generation of one or more sets of labelled DNA fragments, which each terminate with a particular nucleotide base. The fragments must be separated by size to determine the sequence and thus the electrophoretic gels used must be able to distinguish large fragments which differ in size by a single nucleotide. As discussed above, this limits the size of the DNA chain that can be sequenced at one time.

Modifications to the chain termination method have been proposed in the art, for example by combining the enzymatic and readout phases. Thus, instead of a base position being represented by a position on an electrophoretic filter, the base position is provided by a reading taken at a particular point in time. The sequence can therefore be read in realtime. The first technology to use this principle, namely pyrosequencing (Ronaghi, Uhlen and Nyren, Science, 1998, 281, 363-365), does not use fluorophores but luciferase that produces light when triggered indirectly by pyrophosphate released from a polymerisation step where nucleotides are supplied one at a time. The yield of light from this process is much lower than with fluorophores, thus DNA must still be cloned such that each polymerisation step yields enough light for secure detection. This method may process DNA lengths of 400 nucleotides but is not well suited for detecting homopolymers within sequences i.e. repetitions of the same nucleotide.

Other realtime methods include sequencing by synthesis which can be used for multimolecule or single molecule sequencing, sequencing by ligation (for multimolecule sequencing) and sequencing by stepwise ligation and cleavage (for multimolecule sequencing). Sequencing by synthesis involves the use of fluorophore labelled terminating nucleotide bases which are added to an immobilised target DNA sequence. A single terminating nucleotide base is thus incorporated by polymerisation into the target DNA sequence in each cycle and the base is then determined by virtue of its fluorophore label. The terminating base can be chemically neutralised once the readout has been obtained to allow polymerisation to continue. Further, the lipid chain between the base and the label can be cleaved chemically or photochemically so that previously incorporated labels can be removed to allow the reading of subsequently incorporated labels.

Sequencing by ligation involves ligating fluorophore labelled probes to an unknown sequence where the sequence can be determined by the sequence of the probe which is able to ligate thereto. Further, sequencing by stepwise ligation and cleavage (Brenner et al, U.S. Pat. No. 5,714,330, which is incorporated herein by reference) involves a collection of slightly varied methods, based on the use of a probe which has a nuclease recognition site for a nuclease whose cleavage site is separate from the recognition site. Thus, the DNA sequence may be determined either by virtue of the sequence of the probe which binds thereto or by virtue of a label attached to a nucleotide base incorporated into the DNA sequence and the nuclease recognition site in the probe is then able to induce cleavage of the DNA sequence to be determined to release the probe and/or incorporated nucleotide to shorten the sequence to allow determination of the next nucleotide(s).

In the stepwise ligation and cleavage methods of the prior art detection of the base within the sequence relies on detection of the label attached to the probe which binds during the ligation process (either once the label is attached or on its release during the cleavage step). Base detection may be achieved by sequential steps of contacting the target polynucleotide with a labelled probe (specific to one or more bases) and determining if it binds. If it does the cleavage step is then performed. If it does not, the next probe is added until a probe binds. In this way only a single label may be used. This process may be accelerated by using different labels, e.g. fluorophores, which may be used to discriminate between different probes which may all be added together. Binding of a particular label and hence probe allows a determination of the complementary sequence to which it bound allowing the determination of one or more bases of the target sequence.

However, this process requires the generation of multiple different labels and means for their discrimination leading to complex production and detection systems. A rapid sequencing method is therefore required which allows probes to be added together but does not require the use of multiple labels to allow their discrimination and hence may be performed using only a single label and detection system for the sequencing method.

The inventor now provides a new sequencing method in which multiple cleavage enzymes are used in stepwise ligation and cleavage sequencing reactions.

In a first aspect, the present invention provides a method for determining a nucleotide sequence of a polynucleotide comprising the steps of:

(i) contacting said polynucleotide with at least a first and second test probe each comprising a portion which may be complementary to one or more bases in said polynucleotide, and optionally at least one test complementary base each of which may be complementary to a base in said polynucleotide, and covalently binding said first or second test complementary probe to said polynucleotide when said test first or second complementary portion of said test complementary probe is complementary to said one or more bases in said polynucleotide by ligation of said first or second probe to said polynucleotide;

(ii) adding a first enzyme capable of removing at least part of said first test probe and at least one base of the polynucleotide being sequenced by a cleavage reaction if said first test probe bound to said polynucleotide and then sequentially adding at least a second enzyme capable of removing at least part of said second test probe if said second test probe bound to said polynucleotide, wherein each of said enzymes is different and specific for said first or second probe;

(iii) optionally repeating steps (i) and (ii) with at least two different test complementary probes and at least two enzymes wherein said enzymes may be the same or different to the enzymes used in step (ii) until a test probe which has a portion which is complementary to said one or more bases and optionally a test complementary base has bound to said polynucleotide;

(iv) determining which test complementary base and/or complementary portion of the test probe bound to said one or more bases of the polynucleotide by determining whether said test complementary base and/or probe bound to said polynucleotide during steps (i), (ii) or (iii) to identify said one or more bases of the polynucleotide;

wherein each cycle of steps (i) to (iv) is performed one or more times, and in each cycle one or more bases of said sequence are identified.

Preferably the polynucleotide is immobilized on a solid support.

The method allows the identification of one or more terminal end nucleotides of the polynucleotide sequence and one or more nucleotides are removed from the end of the polynucleotide to allow any further desired cycles of ligation and cleavage to occur.

In said method two or more test complementary bases or probes may be used in each cycle. In step (ii) multiple enzymes each capable of cleaving a different test complementary probe may be used sequentially.

In methods in which complementary bases are also employed, these bases may be used to bind to the target sequence at the free 3' end (wherein the probe binds downstream from this site) and may be attached by polymerisation using an appropriate polymerase. The signalling means discussed hereinafter may be associated with the bases or probes, but must be released on cleavage.

Various methods may be used which employ a complementary test base. In the event that the test base is simply used to complete the double stranded section to be cleaved and is not complementary to a base to be sequenced, all 4 possible bases may be used in the reaction at the same time and the sequence is determined based on which test probe binds. In that case in the above method a polymerase is also used in step (i). Since the incorporated base is removed on cleavage with at least a portion of the test probe (preferably all of the test probe), either the base(s) or test probe(s) may carry the signalling means. In contrast, if one of the bases to be sequenced is the base to which the test base binds, since the probe provides the means of determining which probe has bound by whether it has been ligated to the target and is present for cleavage, a first test base should be used with a first test probe such that binding of the first test base can be identified by binding and cleavage of the first test probe. In that case, in step (i) a first test probe and base should be added and ligated and excess removed before a second test probe and base is added and ligated and so on before the cleavage step. In this scenario the signalling means may be attached to either the test base or probe. Conveniently, however, such that the process is as simplified as possible, the base(s) to be detected are complementary to one or more bases in the test probe and either no test bases are used (i.e. the probes bind at the 3' end of the single stranded portion of the target polynucleotide) or all possible bases are used together to complete the double stranded portion of the resulting molecule to allow for subsequent cleavage.

When a complementary base is used, it may carry a signalling means. The complementary base may be a terminating nucleotide added to the end of the extending chain by polymerisation. This base may bind adjacent to the probe which binds to the target polynucleotide.

The at least two test probes to be added, may be added sequentially or together or a combination thereof (e.g. two probes together followed by two further probes). When added sequentially the ligation step may be performed after each addition (which is appropriate when test bases are also used) or preferably is performed once all test probes have been added. As discussed below, more than four probes may be used in the method which all may be added sequentially and/or together.

In a preferred feature, in step (i) at least a first, second, third and fourth test probe each comprising a portion which may be complementary to one or more bases in said polynucleotide is used and in step (ii) at least a first, second, third and fourth enzyme is used, all of which enzymes are different and specific for said first, second, third or fourth probes.

In one preferred embodiment in each cycle one base is identified.

In an alternative preferred embodiment in step (i) at least a first and second test probe each comprising a portion which may be complementary to one or more bases in said polynucleotide is used and in step (ii) at least a first and second enzyme is used. Preferably in each cycle more than one base of said sequence is identified.

In methods in which only a first and second test probe is used, it is possible that a probe with complementarity to the target polynucleotide may not be used and thus a probe may not bind in step (i). In that case step (ii) is redundant and optionally is not performed. However, in automated methods such a step may be performed before step (iii) in which a complementary probe will ultimately be bound. Nevertheless, in methods in which step (ii) is not performed, e.g. in a first part of a cycle, necessarily steps (i) and (ii) will be performed in the next part of the cycle when different probes are used until a probe binds to the polynucleotide.

In a preferred aspect, steps (i) to (iv) are repeated more than once, i.e. more than one cycles are performed, preferably at least 2 cycles as discussed hereinafter. In a particularly preferred aspect, said steps are repeated such that all test base or probe sets are tested.

Hence, the method of the invention determines whether a particular nucleotide or probe has been incorporated into a polynucleotide to be sequenced, where the binding of the test probe or base (which is preferably labelled) indicates the incorporation of a particular test complementary nucleotide or probe and thus the sequence to which it bound in the polynucleotide can be identified. Said one or more bases which are identified may be the one or more bases to which the test probe bound and/or one base to which the test base bound.

The term "determining a nucleotide sequence" as used herein refers to the determination of a partial as well as a full sequence. (This phraseology is used interchangeably with "identifying" a base or bases in a sequence.) Any sequence length is encompassed by the determination of a nucleotide sequence, hence, at least one nucleotide base may be determined by the method, although preferably more than one nucleotide may be determined e.g. at least 2, 3, 10, 20, 30, 40, 50, 60, 70, 80, 90, 100, 200, 300, 400, 500, 600, 700, 800, 900, 1000, 2000, 4000, 6000 or 10000 or more nucleotides may be determined. Thus, preferably the steps of the method, (i.e. each cycle) are performed at least 2, 3, 10, 20, 30, 40, 50, 60, 70, 80, 90, 100, 200, 300, 400, 500, 600, 700, 800, 900, 1000, 2000, 4000, 6000 or 10000 times or proportionally lower if multiple bases are determined in each reiterative cycle.

Determination of the nucleotide sequence includes the identification of the specific base at a particular position (i.e. A, T/U, G or C), i.e. absolute identification, or provides partial identification of that base, e.g. the method may identify a set of bases, of less than 4, (i.e. 3 or 2) which consists of the options for that base, e.g. A or T, but not G or C, or A, T or G but not C. Alternatively the partial identification provides information on the identity of the base which when coupled with information obtained, e.g. in other cycles, allows absolute identification of the base. Such partial identification in a cycle is especially useful when more than one base is to be identified (i.e. read) in each cycle, i.e. when the number of probe bases contacting the target which are not fully degenerate in the probe sets is two or more. The partial identification which is obtained may be especially useful if the "step size", i.e. the number of bases progressed in each cycle is less than the number of bases involved in the reading (e.g. two bases are identified per cycle, but the target sequence progresses, e.g. is shortened, only one base at a time, for example in the stepwise ligation and cleavage method, cleavage may remove a single base from the target sequence before the next cycle). A combination of the information obtained from overlapping readings may be used to obtain the sequence unambiguously or close enough to unambiguously to be useful, especially when the individual that is the source of the sequencing material belongs to a species for which the genome mapping is known, and primarily single nucleotide polymorphisms (SNP) data is the aim of the sequencing. The fact that each base will be involved in at least two reading cycles may, with the right combination of probe sequences in the probe sets, be used to enhance the information level to increase the data quality, e.g. to identify the base in instances for which the ligase has the lowest selectivity with higher certainty without the need for a high number of probe sets.

Thus, by way of example, for two bases identified in each cycle, but one base step size, 4 probe sets can be used instead of 16, and still the base sequence may be identified with higher quality of SNP data, in nearly all cases when the genome map is known. In this case, in each of the probe sets 4 different types of probes are present though not distinguished. Thus in the first cycle it can be established that the target two base sequence has 4 possibilities based on the probe set which contains the probe that binds. In the next cycle, similarly 4 possibilities can be identified for the target two base sequence. However, in these two cycles the same base is read in both cycles as the sequencing reaction steps forward only one base between cycles. This overlapping information can be combined and improved as sequencing continues to identify the sequence by identifying which of the 4 possibilities that bound is the correct one in light of information revealed in subsequent cycles.

Similarly, when 3 bases are involved in the reading cycles, but only one base step size, e.g. 9 probe sets can be used instead of 64. As all bases in this way have been involved in 3 readings, a single reading fault will in most cases be detected, especially if the genome map is known. In addition double faults may also quite often be detected with the right construction of the probe sets, especially in those cases for which the ligase is least specific, i.e. for T4 DNA ligase the T/G specificity.

Thus, a "cycle" as referred to herein refers to the steps required to achieve binding of a test base or probe to the target sequence in which step (i) to (iv) above are performed and identification of said base(s) may be partial or complete at the end of that cycle.

Further, "determining a nucleotide sequence" includes resequencing known nucleotide sequences, as well as sequence comparisons and investigating polymorphisms and mutations in known sequences. Additionally, "determining a nucleotide sequence" may encompass determining the positions of one, two or three of the four types of nucleotides in a sequence, for example, it may be desirable to only determine the position of cytosines within a sequence, as well as identifying the positions in the sequence of any or all of the four nucleotide bases.

The "polynucleotide" whose sequence is determined in the method of the invention may be any polynucleotide but is preferably a DNA or RNA sequence. Typically, RNA sequences are subjected to reverse transcription to produce copy DNA before being subjected to sequencing. Alternatively, if an RNA sequence is to be used directly in the methods of the invention, reverse transcriptase/RNA polymerase or RNA ligase may be used to incorporate the complementary base or the probe as discussed further below, rather than DNA polymerase or DNA ligase which would be employed for a DNA sequence. The polynucleotide sequence may further be any length but comprises at least two nucleotide bases and generally at least 3, 4, 5, 6, 7, 8, 9, or 10 nucleotide bases. For example, polynucleotide sequences of at least 100, 200, 300, 400, 500, 600, 700, 800, 900, 1000, 2000, 4000, 6000 or 10000 bases may be examined using the present invention.

Whilst in a preferred embodiment multiple polynucleotide sequences (i.e. multiple molecules) are used to generate sequence information and the information from the signalling means e.g. labels, attached to each molecule is combined, in an alternative embodiment the polynucleotide to be sequenced is a single polynucleotide. As referred to herein, a "single" polynucleotide refers to an individual molecule for sequencing by the method described herein. In this case, the data of a single molecule is used to derive the sequence. In this embodiment, where desired more than one molecule may be sequenced simultaneously using the method, but in that case each single polynucleotide's base(s) are identified separately. The method in this embodiment relies on the use of a signalling means that produces a signal that is detectable even when only a single signalling means, e.g. label, is present, e.g. a single bead, as discussed hereinafter.

As referred to herein, "immobilised" refers to direct or indirect immobilisation to a support, for example, by binding to another molecule, which is bound to the support. Direct immobilisation may be achieved by chemical coupling and indirect immobilisation may be achieved for example by coupling through binding partners, as described hereinafter, e.g. by hybridisation to a complementary oligonucleotide, e.g. through linking molecules. This form of indirect coupling is preferred.

Hybridisation may be followed by ligation to avoid release of target polynucleotide at elevated temperatures or applied forces, especially if the region of hybridisation is short.

The "solid support" may be any solid support, for example a slide e.g. a glass slide, microarray, microparticle etc but particularly may be an apparatus adapted for detecting a signal, e.g. for detecting a bead as described further below e.g. as identified in PCT/GB2010/00324, which is hereby incorporated by reference (i.e. a chip for optical detection or for magnetic detection). Where necessary, the solid support, e.g. chip, may be modified to allow appropriate binding of target polynucleotides, e.g. to allow binding at specific sites to allow performance of the method and detection of a signal, e.g. a bead.

As discussed above, the test complementary base or the probe is bound to the polynucleotide whose sequence is to be determined (target sequence). Hence, preferably, the polynucleotide sequence of the invention may be at least partially single stranded to allow the binding of the complementary base or the probe. Particularly, the polynucleotide sequence may be single stranded with a complementary oligonucleotide sequence attached 5' to the polynucleotide portion whose sequence is to be determined, providing a primed polynucleotide sequence which can be extended e.g. by the incorporation of complementary bases by polymerisation as well as allowing binding of the probe. Alternatively, the polynucleotide may be mostly double stranded, for example, double stranded with a single stranded protrusion or portion of a few nucleotide bases, e.g. 2, 3, 4, 5, 6, 7, 8, 9, 10 or more nucleotide bases to which a probe may bind by ligation, e.g. a complementary double stranded probe with a complementary overlap. As discussed below, probes may be single stranded or may be double stranded with single stranded protrusions which may bind to a part or all of the single stranded protrusion in the polynucleotide sequence.

"Contacting" as referred to herein refers to bringing the polynucleotide and test base or probe into contact under conditions that allow formation of complementary base pair binding if the test probe or base has complementary bases to the one or more bases in the polynucleotide.

Covalent binding may be achieved by any method or technique which allows the binding of a base or probe to its complementary sequence in the polynucleotide sequence. Particularly, a single base may be incorporated by polymerisation e.g. using DNA or RNA polymerase, or transcriptase I reverse transcriptase, and the probe is incorporated or bound by ligation. Such incorporation of the base or probe will extend the polynucleotide either in the 5' to 3' or 3' to 5' direction.

"Ligation" as used herein refers to the formation of a covalent bond or linkage between the terminal ends of two or more nucleic acids in a template driven reaction where the ligation may occur enzymatically or chemically. Ligation may be achieved using DNA ligase for DNA sequences and RNA ligase for RNA sequences.

The term "base" or "nucleotide" as used (interchangeably) herein includes the natural nucleotides of adenine, guanine, cytosine, thymine and uracil, particularly in the 2'-deoxy form or non-natural nucleotides which function in the same way, i.e. form a complementary base pair with a natural nucleotide and can be incorporated into a polynucleotide sequence by polymerisation or ligation.

Reference to a "complementary base" refers to a base which specifically base pairs with a base to be identified in the polynucleotide. Thus, an incorporated complementary base will be an adenine if the base to be identified in the polynucleotide is a thymine or will be a guanine if the base to be identified in the polynucleotide is a cytosine and vice versa.

The "portion" of the probe "which may be complementary to one or more bases in said polynucleotide" refers to a sequence of one or more nucleotides or bases which is capable of binding to the target polynucleotide when they are complementary.

A "test" complementary base or probe refers to a probe or base which may exhibit the desired complementarity to the target sequence. As described hereinafter, a limited number of permutations are possible, for example for a single base only 4 permutations are possible. Test bases or probes are used to present different permutations to establish if the base or probe has complementarity to the target sequence and hence will bind to that sequence. Test bases or probes without the desired complementarity will not bind to the target sequence.

As referred to herein said "at least a first and second test" probe allows for the inclusion of multiple different bases or probes at one time (e.g. 2, 3, 4, 5, 7 or 8 or more bases and/or probes). Such different bases or probes are different in the base or portion of the probe which may be complementary to the one or more bases under investigation. Identification of which base or probe has bound to the target polynucleotide is achieved by the use of different cleavage enzymes which selectively cleave only one of the probes used and thereby releases a signalling means which may be detected. Alternatively, partial information on the identity of the probe may be obtained which may be coupled with information obtained in later cycles as discussed hereinbefore. Identification of bases on the basis of cleavage reactions may be coupled with identification of bases on the basis of the signalling means (e.g. using the same or different signalling means) as described hereinafter.

The probe used in the ligation reaction should be capable of being ligated to the target polynucleotide and should form a duplex with the polynucleotide before the ligation when complementarity exists. Preferably, the probe (or the region thereof which binds to the polynucleotide) should be perfectly matched to the polynucleotide to allow successful identification of the polynucleotide sequence i.e. the probe should have 100% complementarity to the sequence to be identified.

The probe may comprise at least 2, 3, 4, 5, 6, 7, 8, 9, 10, 15, 20, 25, 30, 40 or 50 nucleotides. In the event that the probe is double stranded, each strand may comprise this number of nucleotides. The probe may also comprise a signalling means, as discussed further below.

The probe may be single stranded or may be at least partially double stranded, depending on the specific method in which it is to be used. Preferably, probes for use in the invention's stepwise ligation and cleavage methods may be at least partially double stranded. Particularly preferably said test probe comprises a double stranded portion which may contain a recognition site for a nuclease and may further have a protruding strand (or single stranded part) which can form a duplex with a complementary protruding strand of the polynucleotide. In this way, probes will ligate to polynucleotides which have complementary protruding parts. The polynucleotide sequence may be determined either by virtue of a signalling means attached to the test probe, or by virtue of a signalling means attached to a nucleotide base which is incorporated into the polynucleotide prior to the ligation step. In either case, after ligation of the probe, a cleavage is conducted, e.g. by a nuclease recognising a sequence within the probe to cleave the ligated complex at a site one or more nucleotides from the ligation site along the polynucleotide, leaving an end which may participate in any further cycle of ligation and/or polymerisation and release the signalling means (with associated nucleotides) to allow its removal.

In this aspect, the probe may be double stranded with a protruding single stranded portion, for example of at least 1, 2, 3, 4, 5 or 6 nucleotide bases, which may be complementary to all or part of a protruding single stranded portion of a polynucleotide sequence. To achieve ligation, preferably said probe has a single stranded portion of 3 or more bases, e.g. 4, 5, 6 or 7 bases. Thus, it is not critical whether the protruding strand of the probe is a 5' or 3' end, as long as it is capable of ligating to the protruding strand of the polynucleotide. Preferably, the protruding strands of the polynucleotide and the probe form a perfectly matched duplex.

In accordance with the invention, the probe may be cleaved by an enzyme specific to that probe. Thus, conveniently the probe contains at least one recognition site for a cleavage enzyme.

The "enzyme capable of removing at least part of said test probe" is a cleavage enzyme which recognizes and binds to the test probe when bound to the target nucleotide sequence and cleaves the test probe and/or a sequence adjacent to said probe on the target polynucleotide, but may not necessarily bind to or cleave said test probe when not bound to the target nucleotide sequence. When said enzyme cleaves the test probe, the cleavage effectively cleaves and hence removes the cleaved part of the probe from the target polynucleotide: probe complex. When said enzyme cleaves an adjacent sequence, the cleavage occurs upstream or downstream of said probe such that the probe (in its entirety) and some of the target polynucleotide sequence is removed from the target polynucleotide:probe complex on cleavage. The cleavage and recognition sites are preferably separate. Whilst the recognition site consists of at least a portion of the probe sequence, the cleavage site may not contain any of the probe sequence, e.g. when the cleavage site is up or downstream of the recognition site, e.g. when the enzyme is a restriction enzyme.

When the probe carries a signalling means such as a label, the cleavage site may be between the label and the rest of the probe which binds to the target polynucleotide to be sequenced. In that case, if necessary, to allow reiterative sequencing reactions, a further cleavage enzyme may be necessary to remove the remaining portion of the probe and at least a part of the target sequence to reveal a new base(s) for sequencing. Conveniently, however, the cleavage site is located such that on cleavage the probe is removed in full from the target polynucleotide:probe complex as well as at least one base of the target polynucleotide.

Preferably said enzyme is a nuclease, e.g. a restriction enzyme, which has a cleavage site separate from its recognition site and said probe contains a recognition site for said nuclease. In this case cleavage results in the removal of one or more bases from the target polynucleotide. This allows the method to be repeated. Each test probe (or probe set) has a recognition site for a different nuclease.

Thus in a preferred aspect, the probe may further comprise a nuclease recognition site for a nuclease (restriction enzyme) which allows nuclease cleavage at a position remote to the recognition site. Preferably, for use in stepwise cleavage and ligation reactions, said nuclease is a type IIb restriction enzyme, preferably AloI, ArsI, BaeI, BarI, BpiI, Bsp24I, FalI, Hin4I, NmeDI, PpiI, PsrI or TstI, or a type IIs restriction enzyme, preferably AarI, Acc36I, AceIII, BbsI, BfuAI, BtgZI, Eco31I, EcoO441, EspI, FokI or LweI.

For example, the nuclease recognition site may allow cleavage by a nuclease at least 1, 2, 3, 4, 5, 6, 7, 10, 15 or 20 bases up- and/or down-stream from the nuclease recognition site. This may be considered the "reach" of the cleavage enzyme. In ligation and cleavage methods described herein, preferably said nuclease generates a long overhang (single-stranded region) on cleavage for the next cycle. Preferably restriction enzymes of type IIs or type IIb are used. In this regard, especially said nuclease is a type IIb restriction site which on cleavage yields a 5-bp overhang.

As is known in the art, in methods reliant on the introduction of a restriction site for cleavage, sequencing may be affected if the restriction site appears in the target sequence. This problem can be avoided by cleaving the targets with the restriction enzymes to be used or ones with the same recognition sequence before the targets are immobilized. Alternatively this problem may be avoided by methylation of the target sequence.

In the method of the invention, at least a first and second probe is employed with a first and second enzyme specific for the respective probes. Thus the first probe recognizes and cleaves the first (but not second) probe when that probe binds to the polynucleotide to be sequenced, i.e. it is specific for the first probe and does not recognize or cleave the second probe. Conveniently this is achieved by using enzymes (and corresponding probes) with different recognition sites. Thus, in a preferred embodiment of the invention, each enzyme is a nuclease which has a cleavage site separate from its recognition site and said test probe contains a recognition site for said nuclease and each enzyme used in said method has a different recognition site. The cleavage site of the enzymes may be the same or different. Preferably, as discussed above, said enzyme is a restriction enzyme, preferably a type IIb restriction enzyme and each enzyme used in said method is a different restriction enzyme.

As discussed above, a portion of one of the test probes covering all permutations in the target sequence is complementary to one or more bases in the polynucleotide. Thus, the probe should be capable of being ligated to the polynucleotide to allow its incorporation therein. Identification of one or more bases in the polynucleotide may then be possible. The portion of the relevant test probe which is complementary to one or more bases is found within the single stranded part of any probe i.e. the part which can ligate to the polynucleotide. In a partially double stranded probe, the complementary portion is found in the single stranded protrusion. Preferably, the single stranded portion of the probe will have 100% complementarity with a corresponding region in the polynucleotide, although this is not necessary. For example, in embodiments where only a single nucleotide is to be identified with a probe, perfect base pairing is only necessary for identifying that particular nucleotide. Typically, in such cases, the terminal nucleotide of the test probe which is incorporated, e.g. ligated to the polynucleotide, will be complementary to the base to be identified in the polynucleotide, though the complementary nucleotide may not be at the terminal end of the probe.

If more than one nucleotide is to be identified in the polynucleotide in each cycle, at least 2, 3, 4, 5, 6 etc nucleotides of the probe which successfully ligates with the polynucleotide will be complementary to those in the polynucleotide. As discussed hereinafter, in such a case it will be necessary to produce sufficient probes to cover each permutation.

Each of the test probes may be tested for successful ligation with the polynucleotide in order to allow identification of the probe which ligates and thus the sequence of the target nucleotide in the polynucleotide.

Therefore, although in a preferred embodiment, the single stranded parts of the probes which will successfully ligate to the polynucleotide may be 100% complementary thereto, it is possible that the single stranded portions of the probes only share at least 80, 90 or 95% complementarity thereto.

As referred to herein "probe sets" refer to a group of probes which are required to identify one of the possible permutations present in the target sequence. In a method of the invention, a probe set may be used as a test probe (e.g. when more than 4 probes are to be used, such as when 2 bases are to be identified in each cycle 4 probe sets are generated and the probes in each set may be discriminated such as on the basis of their signalling means) and thus a probe as referred to herein includes a probe set. A probe set may also be generated if only a single base is to be identified to allow binding of a test probe to an unknown target sequence. In order to identify a particular sequence within the polynucleotide, a set of probes for each permutation should be produced, representative of the total different combinations of bases which are possible within a probe of a particular length. A probe set for each permutation is generated though these probe sets may be used together if each probe set is distinguishable after contact with the target, e.g. via its label or release. If only one base is to be sequenced in the target polynucleotide then only 4 permutations are possible and in that case only 4 sets of probes should be generated. If two bases are to be sequenced at the same time, then 16 permutations are possible in that case and 16 sets of probes should be generated in order to have full specificity.

For example, a probe of 2 nucleotide bases may have 16 different combinations of nucleotide bases and hence 16 different probes should be constructed for addition to the polynucleotide sequence. Probe sets may be generated for each permutation if the probe is longer than the number of bases to be detected in each cycle.

However, probe sets may be combined in the methods of the invention if they can be discriminated, e.g. by using different signalling means as well as different cleavage recognition sites, as discussed hereinafter. Thus, the different probe sets may be added together or sequentially to each other and the presence of a signalling means investigated after (and optionally also before) cleavage. In this aspect, the detection of a particular signalling means may indicate the incorporation of a particular probe and thus the corresponding sequence in the polynucleotide. In methods in which the signalling means is also used to provide sequence information, as discussed hereinafter, and the signalling means is the same in all cases, probe sets are added sequentially to allow detection of the signalling means attached to the probes which have bound to the target polynucleotide.

Preferably the number of bases in the probe (or the single-stranded portion of the probe) are higher than the number read, e.g. a probe of 5 bases may be used in a cycle in which only the identity of the first base is determined. When the probe (or single-stranded portion thereof) is longer than the number of bases to be sequenced in each cycle, to allow binding to the target sequence, variation in the bases which are not complementary to bases to be sequenced is required. Thus degenerate or wobble bases may be used at these positions. Thus for example, if only a single base is to be determined, but the probes (or the single stranded portion of the probes) are 6 bases in length, degenerate or wobble bases should be used in 5 base positions. In this case there are 4 permutations which are possible but a set of probe covering degenerate bases is required for each permutation. Thus, in this case, the 4 sets would comprise ANNNN, TNNNN, CNNNN and GNNNN in which each of these sets would contain 4×4×4×4=256 different probes. This provides sets of probes degenerate in the positions not being read. In this case the readout from the method will be the base present at every fifth position. To identify the intervening 4 bases, the reaction may be repeated by releasing the synthesised strand and restarting the process at another start point, such that the sequence is conducted 5 times in total to provide the full sequence. When used with the stepwise ligation and cleavage method the reading will progress one or more bases in each cycle, depending on the reach of the cleavage enzyme.

The base or probe bound to the polynucleotide may have a terminating effect preventing further extension or incorporation of other bases or probes into the sequence. Thus in a preferred aspect of the method of the invention the complementary base or probe is terminating on the binding of further complementary bases or probes.

The base may therefore be a dideoxynucleotide or the probe may have such a base in a terminal position. Such a base is only appropriate in the final sequence cycle as introduction of this nucleotide leads to a permanent termination. For terminations during the sequence reaction and preceding the final cycle, alternative known reversible modifications may be used. In this case, once the incorporated base or probe has been detected by virtue of its signalling means, e.g. the bead attached thereto, the terminating effect can be chemically neutralised, allowing further incorporation or binding of a base or probe to the polynucleotide sequence. Terminations of this sort are known in the art, e.g. modifications to the 3' OH group such as in Jingyue et al. US 2004/0185466, FIG. 14. These terminating groups may be cleaved at the end of the cycle to allow continued polymerisation (see Jingyue et al: PCT/US02/09752 which refers to suitable reagents for doing so). In the case of probes which are added for ligation methods, these probes essentially terminate the reaction (e.g. until the cleavage reaction takes place) and thus no terminating nucleotides are required on said probes though terminating bases may be used, e.g. in which the 5' is dephosphorylated. This may be reintroduced for the next cycle by use of an appropriate kinase.

The terminating effect of the probe may be removed by cleavage of the labelled probe, for example by a nuclease (e.g. a restriction enzyme such as a nuclease or RNA endonuclease).

In a preferred aspect, binding of the complementary probe or base may have a terminating effect if a large signalling means, e.g. a bead, is selected such that its size, e.g. radius is larger than the length of the target polynucleotide. In that case a second signalling means carrying a probe or base is unable to access the target polynucleotide essentially terminating any further extension or binding. In this way even homopolymers may be identified correctly, provided that if multiple bases or probes are carried on a single carrier which acts as a label, e.g. a bead, the bases on the carrier are placed so that two consecutive bases cannot be incorporated on the same target from the same carrier. An advantage with such a method is that there is no need for fluid exchange, or the fluid may be reused directly.

If the polynucleotide is contacted with test bases or probes that fail to bind due to lack of complementarity, different test probes (i.e. with a different test complementary base or portion of the probe) may be used until a test base or probe binds to the polynucleotide, i.e. step (iii) above may be performed. Assessing whether bases or probes have bound to the polynucleotide may be performed at various points during the method, as described hereinafter, by assessing the presence of a signalling means, particularly, before and/or after any test base or probe is contacted with the polynucleotide and/or before release and removal of the signalling means.

"Determining which test complementary base and/or complementary portion of the test probe bound . . . by determining whether said test complementary base and/or probe bound to said polynucleotide during steps (i), (ii) or (iii)" as defined herein refers to assessing whether the base or test probe bound during the process. Conveniently one may assess the presence or absence of a signal from a signalling means associated with the target polynucleotide during steps (i) to (iii) which indicates that the test base or probe bound to the polynucleotide. As used herein said signalling means which is "bound" to said polynucleotide binds via the intermediacy of a test probe or base.

Thus, for performance of the method of the invention, a signalling means is associated with said test probe or test complementary bases. A "signalling means" is any moiety capable of direct or indirect detection by the generation or presence of a signal. The signal may be any detectable physical characteristic such as conferred by radiation emission, scattering or absorption properties, magnetic properties, or other physical properties such as charge, size or binding properties of existing molecules (e.g. labels) or molecules which may be generated (e.g. gas emission etc.). Techniques may be used which allow signal amplification, e.g. which produce multiple signal events from a' single active binding site, e.g. by the catalytic action of enzymes to produce multiple detectable products.

Conveniently the signalling means may be a labelling means (e.g. a label) which itself provides a detectable signal or a means for generating a detectable signal. Conveniently this may be achieved by the use of a radioactive or other label which may be incorporated during probe production or conjugated directly to bases or probes to be used in the invention.

Thus in a preferred aspect the signal is provided by a labelling means associated with said test probe or test complementary base, which is preferably attached to said test probe or test complementary base.

Appropriate labels are those which directly or indirectly allow detection or measurement of the binding of the probes or bases to the target polynucleotide. Such labels include for example radiolabels, chemical labels, for example chromophores or fluorophores (e.g. dyes such as fluorescein and rhodamine), or reagents of high electron density such as ferritin, haemocyanin or colloidal gold. In one aspect the label to be used is not a bead. However, in a particularly preferred aspect the label is a bead.

Alternatively, the label may be an enzyme, for example peroxidase or alkaline phosphatase, wherein the presence of the enzyme is visualized by its interaction with a suitable entity, for example a substrate. The label may also form part of a signalling pair wherein the other member of the pair is found on, or in close proximity to, the probe or base which binds to the target polynucleotide, for example, a fluorescent compound and a quench fluorescent substrate may be used on adjacent binding bases and probes.

The signalling means may be associated with the probe or base indirectly e.g. through binding partners one of which carries a signalling means as discussed hereinafter. Thus in a preferred aspect, a first binding partner of a binding pair is attached to said test probe or test complementary base and said signalling means is attached to a second binding partner of said binding pair and said first binding partner is attached to said second binding partner during said method. Thus, for example, a label may be provided on a different entity, such as an antibody, which recognizes a peptide moiety attached to the probe or base, for example attached to a base used during synthesis of the probe. When the signalling means is not directly associated with the probe or base, but the probe or base provides a relevant means for attaching the signalling means, the signalling means may be associated with the probe or base at any convenient point during the process.

Thus in a preferred aspect the method of the invention provides a method for determining a nucleotide sequence of a polynucleotide, preferably immobilised on a solid support, comprising the steps of:

(i) (a) contacting said polynucleotide with at least a first and second test probe each comprising a portion which may be complementary to one or more bases in said polynucleotide, and optionally at least one test complementary base each of which may be complementary to a base in said polynucleotide, to which test base and/or probe a signalling means is attached or to which a first binding partner of a binding pair is attached, and covalently binding said first or second test complementary probe to said polynucleotide when said test first or second complementary portion of said test complementary probe is complementary to said one or more bases in said polynucleotide by ligation of said first or second probe to said polynucleotide, (b) when a binding partner is attached to said test complementary base and/or probe, binding a signalling means attached to a second binding partner of said binding pair to said test complementary base and/or probe to which said first binding partner is attached through said binding pair;

(ii) adding a first enzyme capable of removing at least part of said first test probe and at least one base of the polynucleotide being sequenced by a cleavage reaction if said first test probe bound to said polynucleotide and then sequentially adding at least a second enzyme capable of removing at least part of said second test probe if said second test probe bound to said polynucleotide, wherein each of said enzymes is different and specific for said first or second probe;

(iii) optionally repeating steps (i) and (ii) with at least two different test complementary probes and at least two enzymes wherein said enzymes may be the same or different to the enzymes used in step (ii) until a test probe which has a portion which is complementary to said one or more bases has bound to said polynucleotide and optionally a test complementary base has bound to said polynucleotide;

(iv) determining which test complementary base and/or complementary portion of the test probe bound to said one or more bases of the polynucleotide by determining whether said signalling means attached to said test complementary base and/or probe bound to said polynucleotide during steps (i), (ii) or (iii) to identify said one or more bases of the polynucleotide;
wherein each cycle of steps (i) to (iv) is performed one or more times, and in each cycle one or more bases of said sequence are identified.

The assessment of the presence or absence of a labelling means or the level of signal may be made at various times during steps (i) to (iii) to allow the determination, e.g. (a) assessment may be made before any binding (i.e. at the start of step (i)), (b) assessment of binding after steps (i) or (iii) (part (i)) to determine if a signalling means is bound to the polynucleotide, and/or (c) assessment of binding after cleavage (i.e. after step (ii) or (iii) (step (ii)). Since the method relies on selective cleavage by different enzymes, the determination is made at least after the cleavage step. In methods in which the signalling means provides additional sequence information, the determination is also made at least after the binding of steps (i) or Iiii) (part (i). The assessment may be quantitative or qualitative.

Thus in a preferred aspect the determining step (iv) comprises determining the presence, absence or level of a signal associated with said test probe or test complementary base, wherein the presence of signal is indicative of binding of said test base or probe. In a further preferred aspect the level of signal associated with said test probe or test complementary base before and after said cleavage step is determined and a decrease of signal after cleavage is indicative of binding said test base or probe.

The signalling means are removed during the determining step (iv), e.g. as described hereinafter. The step of determination includes all the actions necessary to achieve the determination, e.g. including cleavage, unless such steps are separately recited.

As mentioned above, various different protocols may be used which allow the determination of step (iv). At its simplest test probes to a single permutation and carrying a signalling means may be added to the target polynucleotide and the presence of the signalling means binding to said target may be assessed to determine if that permutation (i.e. specific base) was present in the target polynucleotide. The signalling means is then released during the cleavage step and the method repeated with test probes to a different permutation until the relevant permutation is identified as evidenced by binding of the signalling means. In this case the signalling means is detected in situ. In the alternative it may be detected on release by cleavage.

In methods of the invention, the release of the signalling means, e.g. label is indicative of the base under investigation e.g. the distinguishing feature between the different probes or probe sets is the ability to be cleaved by a first but not second enzyme (e.g. a specific restriction site in the linkage of the signalling means to the probe or within the probe) and release of the signalling means under relevant conditions (e.g. use of the correct restriction enzyme for a restriction site which releases the signalling means in one of the permutations) is indicative of the target, base(s). In this preferred aspect, said test probes or the linkage between the signalling means and said test complementary probe or base comprises a recognition site for a restriction enzyme.

The invention allows a single signalling means to be used, but in addition, multiple different signalling means may be used which each generate a different type of signal to identify which test probe has bound. Such methods may be used as additional confirmation of the identity of the target base(s) e.g. the bound probe is recognized via both its cleavage characteristics and the signalling means attached to it. Alternatively, such methods may be used to reveal additional sequencing information during the method. When a single signalling means is used, this may be used to identify the probe which bound and which is removed during the cleavage reaction. The signalling means may also be used to provide additional sequencing information as it is independent of the cleavage recognition site. Thus one may generate, for example, 16 probes to cover each of the permutations possible for variation in two bases. These probes may then be grouped into sets in which the first (or second base) is the same but the other base of interest varies, i.e. into 4 probe sets all of which carry the same signalling means but in which the 4 probes of the set may be discriminated based on their cleavage characteristics, i.e. cleavage enzyme recognition site. In the method a first probe set is added and binding of a probe from that set (before cleavage) is assessed. If no probe binds, the second set of probes is added and so on until a probe binds. Once a probe from a probe set binds, this allows the identification of one base in the sequence, based on the identity of the probe set in which the first (or second) base is invariant. To identify the second (or first) base, i.e. the identity of the specific probe which bound from within the 4 probes of the probe set, successive cleavage reactions are performed with each of the different cleavage enzymes until cleavage occurs and the signalling means is released. In this way, both the first and second bases may be identified in a single cycle.

Conveniently, multiple different signalling means may also be used in such a method and in that case all probe sets may be used simultaneously. Thus for example one may determine two adjacent bases in each cycle in which one base is determined on the basis of the signalling means type and the other base is determined on the basis of the cleavage characteristics of the probe. In this case one may generate 16 probes to cover each of the permutations possible for variation in two bases. The 4 probe sets which differ in the first base may be distinguished on the basis of different signalling means and the 4 probe sets which differ in the second base may be distinguished on the basis of their cleavage characteristics. The 4 probe sets may be used together or sequentially in methods of the invention. Thus for example, if the probe sets are used together, and cleaved with different cleavage enzymes sequentially, one may detect the signalling means that is bound and the cleavage enzyme required for cleavage to identify which of the 16 probes bound and hence 2 bases may be sequenced in each cycle.

It will be appreciated that further bases may be identified in a single cycle by using different discriminatory techniques as discussed above and/or sequential addition of the probes or probe sets. By way of example, 3 bases may be identified by using 4 probe sets added sequentially in which each probe in the first probe set (probe set 1) is invariant at position N, but probes for each permutation at positions N+1 and N+2 are provided in the probe set. Within the probe set, the probes which vary at N+1 may be identified by different signalling means for the different variables and the probes which vary at position N+2 may be identified by different cleavage characteristics for the different variables. In the method of the invention probe set 1 is added to the target polynucleotide. If no probe in probe set 1 binds, probe set 2 is contacted with the target polynucleotide and so on until a probe binds. Once binding has occurred, the signalling means of the bound probe is detected followed by sequential cleavage with relevant enzymes. The identity of position N is revealed by the probe set containing the probe which bound, the identity of the signalling means allows identification of position N+1 and the enzyme which cleaves to remove at least part of the probe reveals the identity of position N+2.

Thus, in a preferred aspect, the present method provides a method in which said first and second probes comprise a first and second set of probes and a signalling means is attached to said probes and/or bases and said at least first and second probe sets and/or bases are added consecutively and the signal associated with the signalling means is detected after each addition to determine which test complementary base and/or probe bound to said polynucleotide to determine the sequence of one or more bases of said target sequence, wherein the one or more bases which are identified are different to the one or more bases which are identified by determining which probe is cleaved during step (ii).

In a particularly preferred aspect, the signalling means which are used may be different. In that case the first and second probes and/or bases may be added together and the determination made in a single step. Thus in a preferred aspect, said first and second probes comprise a first and second set of probes and different signalling means (which may be discriminated) are attached to at least two probes of each set of probes and/or test bases and the signal associated with said different signalling means is detected to determine which test complementary base and/or probe bound to said polynucleotide to determine the sequence of one or more bases of said target sequence, wherein the one or more bases which are identified are different to the one or more bases which are identified by determining which probe is cleaved during step (ii). In this case the first or second probe sets are distinguished on the basis of their cleavage characteristics and the probes within the sets are identified on the basis of their signalling means. Conveniently 4 sets of probes are used each comprising 4 different probes to which different signalling means are attached which may be discriminated.

Preferably, to improve accuracy, the level of the signal from said signalling means is detected and may be compared at various time points during the cycle. Conveniently, the signal is detected before and/or after putative binding and/or after cleavage (when detection at least after cleavage is always performed). If the signalling means is also to be used to provide sequence information, the signal must also be detected at least after binding. In a particularly preferred aspect the signal associated with the probe/base is measured before and after said cleavage step and a reduction in said level is indicative of the binding of said base or probe allowing the identification of the target one or more bases by virtue of the base or probes which attached to said bead. Such methods are useful as enzymatic reactions may be incomplete, e.g. ligation or cleavage, by design or default.

In the above methods the presence or absence or level of signal associated with the base or probe is indicative of the base under investigation. Thus in a preferred aspect, step (iv) is performed by determining the presence, absence or level of signal associated with said base or probe, wherein the presence of signal is indicative of binding of said test base or probe. In a further preferred aspect, the level of signal associated with said base or probe before and after a cleavage step is determined and a decrease of signal after cleavage is indicative of said test base or probe.

As mentioned above, in a preferred aspect, the labelling means is a bead. As referred to herein the "signal" of said bead is the signal which is detected, e.g. its magnetism, optical activity, fluorescence, colour and so on, depending on the nature of the bead used.

Thus, in a preferred aspect, the base or probe comprising one or more bases complementary to the base or sequence in the target polynucleotide to be determined is labelled with a bead. The presence of a single bead attached to a base or probe, which has been incorporated in a polynucleotide can be easily detected, as described hereinafter, allowing identification of the complementary base or probe which has been incorporated before and/or after the cleavage step, and thus the base or sequence to which it bound in the polynucleotide. The use of beads as labels in the sequencing reaction provides many advantages over traditional labels in sequencing methods of the art such as fluorophore labels. Firstly, beads are easy to detect since they are larger than fluorophores which enables their use when single molecule sequencing is used. Furthermore, there is no problem with low signal level when using beads as labels. Further, beads may be detected without the use of expensive equipment, for example using an electronic bead detection mechanism in an integrated circuit or based on light or magnetism. Beads are easily and rapidly removed from a reaction, particularly if they are paramagnetic and hence there is no problem with noise when using bead labels, as opposed to fluorescent labels. Furthermore, mechanical cleavage may be used thus avoiding chemical removal as required in some prior art sequencing methods. Thus in a preferred aspect said bead is removed and/or detected by its magnetism.

Beads have not previously been suggested for labelling nucleotides or probes complementary to a base or sequence to be identified in which they are bound to the target sequence during a reiterative sequencing reaction. Particularly, the use of a single bead as a label to determine the identity of one or more nucleotides at a particular position in a polynucleotide in a reiterative sequencing reaction has not previously been disclosed, particularly when the sequence of the target molecule is not known. In particular, the use of beads in methods of the invention in which multiple cleavage enzymes are used has not been previously disclosed. In view of the large size, beads allow the sequencing of a single molecule. The ability to sequence a single molecule obviates any cloning step and the need for amplification. This results in the reduction of work needed to obtain a sequence and further prevents the introduction of unnecessary errors into the polynucleotide.

Beads and other large labels may be used as both a label and as a carrier of test probes or bases, thus multiple probes may be presented on a single bead, e.g. a set of probes, as discussed hereinbefore. Preferably when a set of probes is used, each set of probes is presented on the same carrier, e.g. bead. Each set of probes for the different permutations may be on separate beads or may be present on the same bead as the probes can be distinguished by means other than the signal of the bead, i.e. by the conditions necessary for release of the bead (e.g. the probes of each permutation have a different mechanism which allows for release of the bead, e.g. a specific restriction site which attaches the bead to the probe).

As discussed above, partially double stranded probes with single stranded protrusions may be used in sequencing methods which require stepwise ligation and cleavage. In this aspect, the probe may comprise a nuclease recognition site in the double stranded portion. In this method the probes may carry the signalling means, e.g. bead, for identification of complementary nucleotides in the polynucleotide. The presence of the signalling means, e.g. bead, may be assessed when the probe (if complementary) is attached to the target polynucleotide (i.e. before cleavage) and/or the cleavage reaction may be allowed to take place thereby releasing the signalling means, e.g. bead, and allowing either its detection on release or its absence from the target polynucleotide.

Whilst in a preferred aspect the probe includes the one or more complementary nucleotides to the one or more nucleotides to be detected, the method also encompasses use of signalling means, e.g. bead, labelled nucleotides and a probe which may be ligated to that nucleotide to provide the nuclease recognition site. In that case binding of the signalling means, e.g. bead, may be assessed to see if it is attached to the target polynucleotide before cleavage and/or after cleavage either as part of the released probe or on one or more nucleotides released by the cleavage.

Once cleaved from the probe, the signalling means should be removed from the polynucleotide to allow detection of the signal in the material which has been removed and/or the signal which remains associated with the target polynucleotide. "Removing said signalling means" e.g. bead, refers to spatially separating the signalling means from the target polynucleotide to allow discrimination between a target polynucleotide with which a signalling means is associated after binding of a relevant test base or probe to which said signalling means was attached and a polynucleotide from which the signalling means has been released and removed. Removal is achieved after release of the signalling means after which the signalling means is free to be removed from the location of the target polynucleotide. Release is achieved by the cleavage step of the method. After release the signalling means may be removed e.g. by magnets or fluid flow, as discussed hereinafter, depending on the signalling means.

In a preferred aspect of the invention, when the signalling means used is a bead, a tethered bead may be used. This may be attached to the solid support or to a part of the target molecule or its linking molecule providing it does not affect the sequencing methods described herein. In this method instead of an external supply of beads a tethered bead is associated with each target, in such a way that they have a higher degree of freedom until they are connected to the probe/base which binds to the target sequence. The added restriction of freedom when bound via the probe/base to the target may be due to a shorter length of the target compared to the tether or due to the positioning of the tether compared to the associated target, resulting in a shorter distance and/or a different positioning in relation to some reference position, which could be the detection point when the methods use detectors in a surface.

In methods of this sort, test bases or probes are bound to said target polynucleotide and carry a binding partner to allow the tethered bead (which carries the other binding partner of the pair) to bind to those bases or probes. However, care should be taken to avoid too much direct binding of bases or probes to the beads, i.e. binding to the bead directly at supply, as opposed to first binding to the target while the beads are held at a distance from the targets, then binding to the target as the beads are moved towards the target polynucleotide or freely allowed to move, thereby reaching the target (i.e. each bead reaching its own target). In many cases the binding partners bind much faster with an optimally designed fluid (e.g. a "bind and wash fluid" as used for streptavidin Dynabeads) than with the enzyme buffer used during polymerization or ligation.

In the case of the use of a tethered bead, removal of the bead refers to removal away from the target polynucleotide to allow access for the probes or bases to bind in subsequent steps or the next cycle.

In the above described method, the steps are performed one or more times and in each cycle one or more bases of said sequence are identified. As mentioned hereinbefore a cycle refers to the steps required to identify one or more bases of the target sequence. If all permutations of the complementary base/probe are presented to the target polynucleotide in a single step with e.g. cleavage of different probes with different enzymes allowing discrimination and/or use of different signalling means, i.e. all test probes/bases are used together, the cycle may be completed by performing the steps only once. However, if not all test bases/probes are presented for identifying a base or sequence simultaneously, additional steps may be required to allow identification of the base or target sequence. In that case the methods comprise the steps as set forth above, but in which steps (I), (ii) and (iv) are performed for each set of test bases/probes to be used until identification has been achieved. As noted hereinbefore, identification of the one or more bases may be absolute or partial.

In determining whether a signalling means is attached, detection steps as described hereinbefore may be used. Thus, the presence or absence or level of signal associated with the signalling means may be detected. In particularly preferred aspects according to the invention, a quantitative assessment is made to determine the level of signal (from the signalling means) attached to the polynucleotide.

In methods of the invention, as discussed hereinbefore, the signalling means as well as their linking groups to the base or probe for each permutation may be different and may be distinguishable allowing their addition together and separate detection during the method. In the alternative the signalling means for all test probes may be identical and each probe set may be added sequentially or separately in step (i) until the probe set with the relevant complementary probe or base is employed.

Groups of probe sets may be added together as they may be distinguished in the cleavage step.

Probes may be distinguished on the basis of their signalling means as well as, for example the recognition sites in those probes. Thus for example, different sets of probes may be bound to the same carrier (e.g. bead) or type of carrier, but each or more than one set of probes have a different restriction site. In that case the one or more sets of probes may be added to the reaction and then successive restriction enzymes are used which are directed to specific probe restriction sites. Release by a particular restriction enzyme would be indicative of the relevant probe binding and hence the identity of the target sequence/base. For example, the method may use 2, 3, or more restriction enzymes with the same number of bases in the overhang, in succession, with detection of signalling means associated with the target before and after each addition. In the case of 4 different probe sets, each could be distinguished by a different restriction site and all probe sets could be added at one time followed by successive cleavage reactions. Alternatively two probe sets could be used in two different cycles in which in each cycle two rounds of cleavage with different enzymes could be conducted. Various combinations are possible. For example, ligation could be performed using one set of probes consisting of G and T probes followed by ligation with a mixture of A and C probes. If A and G probes use one restriction enzyme and C and T another, then all four bases may be differentiated after two ligations and two cleavages. Using another grouping, with three ligations and three cleavages it is possible to differentiate nine groups. By appropriate combinations of groups with two or more bases to be detected, i.e. not fully varied, but possibly partly varied, it is possible to increase the data quality specifically where the ligase is least selective, e.g. for TIG detection. As mentioned above, this may be combined with the use of the signalling means to allow further sequence information to be obtained.

As mentioned above, the step of determining which test complementary base or probe has bound by assessing the absence or presence of the signalling means may be conducted at various points in the method. Thus, step (iv) refers to a determination which may be carried out at various time points in the method. However, information on which probe has bound is only revealed when the cleavage step is performed (step (ii)) and the determination is made after the cleavage step. Preferably, however a determination is also made before cleavage, e.g. before binding and/or ligation for comparative purposes. A determination may also be made before cleavage if sequence information may be obtained not only from the cleavage pattern, e.g. if the signalling means is to be used to discriminate between different probes, as discussed hereinbefore.

Various orders for the steps may be used, depending on the probes and enzymes in use. Thus since two or more probes may be discriminated by virtue of their cleavage reaction they may be added together or sequentially before cleavage. Cleavage enzymes may then be added sequentially. In this scenario the detection of the signalling means may be carried out before addition of the probes, after their addition, before cleavage or after cleavage and may be carried out for each probe binding or cleavage step or after multiple probe binding or cleavage steps depending on the protocol in use.

In the methods of the invention, a complementary base or probe is either labelled with a signalling means prior to binding to the polynucleotide or is labelled with a signalling means after binding to the polynucleotide through the use of binding partners. In a particular embodiment, the base or probe is labelled after binding to the polynucleotide. If labelled after binding, a step of removing any unbound signalling means should be carried out prior to the step of determining the presence of a signalling means attached to the bound base or probe. This may be easily achieved for example if the signalling means are beads which are paramagnetic by applying a magnet.

Similarly, if the base/probe is labelled prior to binding, a step should be carried out to remove any unbound base/probe signalling means labelled complexes before the step of determining the presence of a signalling means attached to the bound base or probe.

The labelled probe or base may be detected in situ (i.e. when attached to the target sequence) or detected on release. In the latter case, the sequencing reaction is washed to remove unbound signalling means from the mixture and then the signalling means are released as described hereinbefore by cleavage. The presence of signalling means in the released mix is evidence of the presence of the corresponding complementary base(s) in the target sequence.

Before assessment of the next set of test probes may commence the signalling means must be removed from the target sequence (or from released probes or bases for reuse). In methods in which signalling means are detected in situ, after their detection they must be released (by cleavage) and removed.

As described hereinbefore, signalling means are released during the enzymatic cleavage step. Thus, a cleavage site may be placed between the base or probe and the signalling means. Particularly, a restriction enzyme site may be incorporated between the signalling means and the base or probe. Any restriction enzyme may be used and cleavage may then be achieved using any suitable restriction enzyme for that site. Particularly, a type IIs or type IIb restriction endonuclease may be employed as described hereinbefore. The restriction or cleavage site may be positioned directly adjacent to the base or probe (i.e. at the part of the probe most proximal to the signalling means) to enable the cleavage of the signalling means together with any linker or other binding moiety which may be present or the restriction or cleavage site may be positioned directly adjacent to the signalling means to enable cleavage and possible reuse of the signalling means. A nicking restriction enzyme may be used to release the signalling means. Whilst the method allows the use of an enzyme that cleaves at a site that allows only part of the probe and the signalling means to be removed, in that case a further cleavage step is then required to remove the remainder of the probe. However, conveniently a single cleavage step is performed which removes the full probe with its attached signalling means as well as one or more bases of the target sequence to allow for the next cycle of sequencing to commence.

Thus in a further preferred aspect said probes or the linkage between the signalling means and said test complementary probe or base comprises a recognition site for a restriction enzyme and said enzyme is an enzyme used in said method.

When beads are used as the signalling means they are preferably magnetic allowing ease of removal, for example using a magnet if the beads are paramagnetic. Alternatively removal may be achieved by separation and washing, e.g. using fluid flow, e.g. over a chip. A combination of these techniques may be used. A further bead detection or visualisation step may be carried out after the cleaved beads have been removed to check that all the beads have been successfully removed, before the reaction is resumed e.g. before the chain terminating effect is neutralised and the performance of such a step is preferred.

The term "bead" as used herein refers to a microparticle which is typically but not necessarily a spherical solid support. Although the size of the beads is not critical, they may for example be of the order of diameter of at least 0.05, 0.1, 0.3, 0.5, 1, 1.5, 2, 2.5, 3 or 3.5 μm and have a maximum diameter of not more than 50, 20, 10, 8 or 6 μm. Particularly, beads of 1 or 2.8 or 4.5 or 10 μm may be used in the invention. By diameter is meant size along the longest axis of the bead or along any axis of a spherical bead. "Radius" denotes half of this diameter. In a preferred feature, the radius of said bead is larger than the length of the polynucleotide.

In methods described herein for single polynucleotides only a single probe/base with a single attached bead will bind in each cycle. In that case, reference to "beads" in the plural should be read in the singular or reflects multiple reactions being conducted together but each on a single polynucleotide.

Monodisperse beads, that is those which are substantially uniform in size (e.g. size having a diameter standard deviation of less than 5%) may be used in the present invention as they provide very uniform reproducibility of reaction.

The bead can be made from any material which allows the formation of a suitable solid support. Non-magnetic polymer beads suitable for use in the methods of the invention are available from Invitrogen as well as from Qiagen, Serotec, Merck, Promega, to name a few, Non-magnetic beads may be manufactured from many different materials well known in the art, for example, from plastic e.g. from polystyrene.

However, to aid manipulation and separation, magnetic beads are preferred. The term "magnetic" as used herein means that the bead is capable of having a magnetic moment imparted to it when placed in a magnetic field and thus is displaceable under the action of that field. In other words, magnetic beads may readily be removed by magnetic aggregation which provides a quick, simple and efficient way of separating any unattached beads following incubation of beads with test bases or probes or following their cleavage from the polynucleotide. This provides a distinct advantage over the fluorophores used in many sequencing methods in the prior art.

Thus, the magnetic particles which are unbound may be removed onto a suitable surface by application of a magnetic field e.g. using a permanent magnet.

Magnetic beads comprise magnetically responsive material which responds to a magnetic field, for example, paramagnetic materials, ferromagnetic materials, ferrimagnetic materials and metamagnetic materials. Hence, iron, nickel and cobalt as well as metal oxides such as $Fe_3O_4$, $BaFe_{12}O_{19}$, CoO, NiO, $Mn_2O_3$, $Cr_2O_3$ and CoMnP can be used. The magnetically responsive material may be only one component of the bead, whose remainder may consist of a polymeric material to which the magnetically responsive material is affixed.

The quantity of magnetically responsive material in the bead is not critical and can vary over a wide range, for example, from about 1% to about 75% by weight of the particle as a whole. The range may be from 2% to 50%, from 3% to 25% or from 5% to 15%. The magnetically responsive material can be dispersed throughout the polymer, applied as a coating on the polymer surface or incorporated or fixed in any other manner that secures the magnetically responsive material to the polymer. Hence, the magnetically responsive material may form the nucleus or core of the bead.

The polymeric material that forms the remainder of the bead can be any material that can be formed into a solid bead. Examples of suitable polymers are polyesters, polyethers, polyolefins, polyalkylene oxides, polyamides, polyurethanes, polysaccharides, celluloses and polyisoprenes. Crosslinking is useful in many polymers for imparting structural integrity and rigidity to the bead.

Superparamagnetic beads for example those described by Sintef in EP-A-106873 can also be used which allow the avoidance of magnetic aggregation and clumping of the beads even with high permeability. Further the magnetic particles sold by Invitrogen as Dynabeads are particularly suited to use in the present invention.

A particular advantage of using magnetic beads is that the beads can be "pulled down" onto the polynucleotide which may be immobilised to a solid support, to enable more rapid incorporation of bead labelled bases or probes into the polynucleotide or to enable more rapid binding of the beads to bases or probes which have been incorporated into the polynucleotide but not yet labelled.

The signalling means, e.g. bead, may be attached to the test complementary base or probe either directly or indirectly in any convenient way before or after incorporation into the polynucleotide, according to techniques well known in the art and described in the literature but ensuring that the signalling means if it is large, e.g. a bead, does not prevent access of the probe or base to which it is attached to the target polynucleotide or prevent required reactions to take place, e.g. polymerisation, ligation or cleavage reactions.

Thus, the base or probe may be attached directly to the signalling means, such as a bead. Such attachment may readily be achieved by methods (e.g. coupling chemistries) well known in the art and conveniently, the base or probe may be bound directly to the signalling means. When the signalling means is large, more than one base or probe may be attached such that the signalling means acts as a carrier, e.g. the base or probe may be used to coat the carrier.

Alternatively, the signalling means, e.g. bead, may be indirectly attached to the test complementary base or probe. The base or probe may therefore be attached to the signalling means through one or more other molecules which may be directly attached to the signalling means. These may give rise to a covalent or non-covalent association. In a preferred aspect, the signalling means may carry one or more linking moieties or spacers which have an affinity for the base or probe or for a tag incorporated into the base or probe. Preferably this indirect binding is achieved via binding partners. In this case, the signalling means may conveniently carry or be provided with a binding moiety capable of binding to the base or probe such that binding occurs via at least two binding partners of a binding pair. As referred to herein a "binding pair" refers to a pair of molecules which form a specific and stable interaction. Examples included DNA:DNA, ligand:receptor, antibody:antigen interactions. Such binding moieties are well known in the art e.g. biotin/streptavidin may be used where the base or probe is coupled to a biotin group and the beads are streptavidin coated.

In a preferred aspect the base or probe may be attached to the signalling means by biotin/streptavidin binding or by biotin/avidin binding in which biotin and streptavidin form the binding partners. Hence, streptavidin or avidin coated signalling means, e.g. beads, may be used to bind a base or probe which is linked to a biotin group. Other binding pairs which may be used include digoxigenin:antidigoxigenin.

In a particularly preferred aspect, the base or probe is attached to said signalling means via a linkage (preferably but not necessarily including binding pairs), which is cleavable. This allows release of said signalling means. As mentioned above, in a preferred aspect said cleavable linkage has a restriction site cleavable by a restriction enzyme. Conveniently this may be generated by use of at least partially single stranded oligonucleotides which are binding partners which together form a recognition and restriction site once hybridized.

The test base or probe may be attached to the signalling means prior to binding to the polynucleotide. In this aspect, single or multiple copies of the base or probe may be attached onto each signalling means if size allows, e.g. when the signalling means is a carrier such as a bead. Preferably said signalling means, e.g. bead, carries at least 100, 500, 1000, 10000 or 100000 probes. These probes may be the same or different but are preferably a single set of probes. In the event that different probes are carried on the same signalling means but they are not from a single set of probes (i.e. directed to a single permutation), probes of each set are preferably distinguishable by virtue of their binding pair, e.g. they may be attached via distinguishable cleavage sites. When using non-terminating bases more than one base may be bound to each signalling means but the number should be kept lower to avoid homopolymer incorporation.

Alternatively, the base or probe may first be bound to the polynucleotide sequence before being attached to the signalling means. In this case, the signalling means may conveniently carry or be provided with one of a pair of binding partners as described hereinbefore.

Coloured transparent beads can be used in the methods of the invention as the signalling means and can be detected. One or more different beads of different colours can be used as labels. Therefore, two, three or four different bead colours can be used in the invention when the signalling means is to be used to provide sequence information. Particularly, one or more different bead colours can be used simultaneously and can be detected as described below in further detail. Different bead colours can thus be used to detect whether different test probes or bases have been incorporated into the polynucleotide, for example the four bases to bind to one base to be sequenced may be labelled with four different coloured beads and the colour of the bead attached to the bound base can identify that base and thus its complementary base in the polynucleotide. This is particularly advantageous when all four bases are applied to the polynucleotide at the same time. Therefore, a specific bead colour may specifically identify a particular base or probe. Such a method can be used in conjunction with discrimination of probes and/or bases based on cleavage with specific enzymes as described hereinbefore.

Detection of different colours (as signalling means) may be achieved through their filtering effect on e.g. three or four colours, for which there exist filtering substances with, as far as possible, non-overlapping filter curves. By combining these substances in different amounts, e.g. 10 different amounts, 1000 or 10 000 different signalling means, e.g. beads, may theoretically be differentiated. Due to some overlap of the filter curves, the number may need to be reduced, but 256 different beads may be differentiated, allowing up to 4 bases to be read at any one time by using probes to each of the 256 permutations and additional bases are read by discrimination on the basis of the cleavage reactions.

As an alternative to filtering beads, coloured beads may be produced by marking e.g. coating such beads with a dye e.g. a fluorescent dye. Further, beads of different colour intensities may be used. Preferably, however, in methods of the invention the label carried by the signalling means, e.g. bead, is non-fluorescent.

Different sized signalling means can be used as labels. Labels of 2, 3, 4, 5, 6, 7, 8, 9 or 10 different sizes can be used simultaneously and be detected. Labels, e.g. beads, of different sizes will be able to identify different bases or probes to which they are attached which will be particularly advantageous in a method of the invention in which different bases or probes are added simultaneously to the polynucleotide. The base which is incorporated may be identified by virtue of the size of the label to which it is bound and this information added to sequence information derived from the cleavage reactions.

When using signalling means of different sizes and/or colours as labels for the bases or probes, it may be necessary to label the bases or probes individually prior to binding to the polynucleotide or to use a different linker or affinity binding pair to specifically bind a particular base or probe to a particular signalling means. In the former case, labelling is conducted before the sequencing reaction and each set of probes (e.g. ANNN) or base (e.g. A) is attached to a different signalling means. Multiple probes or bases of each set may be attached to each signalling means to provide up to 256 different signalling means (for example). In the case of labelling after binding to the polynucleotide target, since the variation in signalling means type is limited by the number of unique binding partners that can be accommodated, the number of different signalling means types that may be used is dependent on the number of unique binding partners that can be used. This can be large if unique oligonucleotides are used as the binding partners.

It may be possible to multiplex the method further by using combinations of different bead sizes, colours and/or intensities as well as the different cleavage enzymes as discussed hereinbefore. Hence, different subgroups of signalling means which may be a range of colours, colour intensities and/or sizes may be used in the method of the invention. The detection of such subgroups of signalling means may require the measurement of a variety of different parameters, for example magnetic detection of bead size and light detection of bead colour.

Thus, in each sequencing cycle for each base(s) the different sets of probes or nucleotides to be tested may be added together or separately depending on the detection technique to be used. Thus all test probes or nucleotides may be added together if they may be distinguished by virtue of the different cleavage enzymes (and possibly the signalling means which is attached), e.g. 4 different types of cleavage recognition sites to denote each of the four possible bases. Alternatively the probes may be added separately or in groups if those groups may be distinguished, e.g. 2 sets of 2 in which 2 distinguishable probes are used in each case. In a further alternative of this type, the probes may be added all together or in groups but they may be cleaved separately or in distinguishable groups. Thus in the method of the invention probes with different nuclease recognition sites are used such that release of a signalling means in response to addition of a particular restriction enzyme allows identification of the probe which bound (on the basis of the restriction enzyme used and the signalling means identified) and hence the identity of the target nucleotide(s).

The detection of the signalling means may, depending on the signalling means, be by optical, magnetic, electric or electrochemical means, particularly when the signalling means is bead. For example, the size and therefore presence of a bead may be detected by virtue of a magnetic field. Conveniently the method of the invention is carried out on a chip, i.e. wherein said solid support is a chip. In a particular preferred embodiment, the signalling means (or labelling means) (e.g. a bead) and detection of the signalling or labelling means may be carried out using an apparatus comprising a surface which is provided with a means for detecting a signalling or labelling means.

This method is principally described below in relation to beads, but may also be applied to other signalling means which are of a large size and which may be detected on the surface by the techniques described hereinbelow. The surface may comprise one or more elements which provide an output dependent on the presence or absence of a bead. In a preferred embodiment, the detection of the bead may be carried out optically by a method described in. PCT/GB2010/00324 for example using an apparatus described therein.

In such a method, the polynucleotide may be attached to the surface which is provided with a means for detecting a bead. Thus, the surface may be provided with one or more light sensitive elements wherein each light sensitive element is arranged to detect a bead adjacent thereto. Thus preferably in said method said surface is provided with one or more sensory elements, preferably light sensitive elements.

The light sensitive elements may alternatively be replaced or used in conjunction with other elements which are capable of detecting a bead e.g. Hall elements. The one or more light sensitive elements provided on or within the surface are capable of outputting a signal which is dependent on the presence or absence of a bead and the signal provided from each light sensitive element will therefore indicate whether a bead and thus an incorporated base or probe is present. In this detection method, the bead is itself directly detected by the one or more light sensitive elements. The bead may be arranged to emit light which can be detected by a light sensitive element e.g. it may be fluorescent, although in a preferred aspect, the bead is detected when it blocks light from reaching the light sensitive element in question. Thus preferably said detection is by detecting light changes resulting from the presence of the signalling means, e.g. bead on a light sensitive surface.

Thus, the bead effectively casts a shadow on the element. The light source used may be ambient light or a dedicated light source may be provided. By illuminating the surface, the detection of any shadows created by the presence of beads or the obstruction of light from the light sensitive elements can be detected more easily. Further, to prevent external light sources from affecting results, preferably the light sensitive elements are shielded from external light by a suitable housing.

The light sensitive elements are therefore capable of measuring the amount of light received by the surface which can determine the presence or absence of a bead. A bead can be detected by an individual light sensitive element or by a group of light sensitive elements, depending on the size of the beads, the light sensitive elements and the distance of the beads from the surface. Hence, it is possible that an individual light sensitive element can detect a bead or that 2, 3, 4, but more likely 4, 9, 16 or more light sensitive elements can detect a bead. The amount of light detected by each light sensitive element and hence the signal output from the light sensitive elements when no beads are present can be used as a reference point against which other measurements can be compared. A reduction in light (i.e. created by the shadow of bead) received by a light sensitive element will result in the output of a signal which differs from that outputted when beads are absent. As discussed below, the amount of light received by each light sensitive element when a bead is present will depend upon various factors, including the bead size, the size of each light sensitive element and the length of the polynucleotide attached to the surface.

The "surface" is preferably provided with a plurality of light sensitive elements arranged to form an array. The light sensitive elements may be on or form the outer layer of the surface or may be comprised within the surface e.g. may be present beneath one or more other material layers. Arrays of light sensors or of light sensitive elements are well known in the art and include charged coupled devices e.g. of the type used in cameras or CMOS active pixel sensors. Modifications may be made to such CCD or CMOS image chips as discussed further below. The surface may be the substrate of such a device.

The polynucleotide whose sequence is to be determined may be attached to or placed above the one or more light sensitive elements present in or on the surface to enable the generation of an output from the attached bead. Preferably, a single polynucleotide may be associated with a light sensitive element or a group of elements and may be detected. A polynucleotide sequence may further be divided over more than one light sensitive element or group of elements to enable the sequence to be ascertained more rapidly i.e. for portions of the sequence to be determined by different light sensitive elements, but in each case a single polynucleotide is sequenced.

The bead may cast a shadow on the surface and on a light sensitive element or a group of light sensitive elements when the bead is present and hence reduce the amount of light received by the light sensitive element(s). For example, the bead may reduce the amount of light received by the light sensitive element(s) by from about 10-100%, e.g. particularly at least 10, 20, 30, 40, 50, 60, 70, 80, 90 or 95%. It will be appreciated that the output provided will be dependent on the size of bead used, the size of the individual light sensitive elements present on the surface and the distance from which the bead is tethered from the surface. Therefore, a bead which is the same size or larger than a light sensitive element may prevent most light from falling on the light sensitive element. Each light sensitive element and bead size combination may be calibrated by measuring the signal output when a bead is present or attached to that light sensitive element.

It is possible for a particular bead size to be chosen depending on the size of the light sensitive elements in or on the surface. Particularly, for the sequencing of a polynucleotide where the 4 bases and/or different probes are added sequentially to each other, a bead may be selected which corresponds to the size of the one or more light sensitive elements in or on the surface. Alternatively, for the sequencing of a polynucleotide where all 4 bases and/or different probes are added simultaneously to the polynucleotide and where the bases or probes are distinguished based on their cleavage enzyme (as well as optionally their bead size), the bead sizes will preferably be smaller than the size of the element or group of elements. Hence, a bead may be selected which when attached to the surface will reduce the amount of light by at least 10, 20, 30, 40, 50, 60, 70, 80, 90 or 95%. For example, 1 µm diameter beads may be used in combination with 1.75×1.75 µm light sensitive elements or 2.8 µm diameter beads may be used with 3.2×3.2 µm light sensitive elements.

Different colour beads may be detected on the surface by each light sensitive element by illuminating the surface with light of different colours. Hence, two, three, four or more different colour beads can be detected by the surface by illumination with different colour light. The surface may be capable of providing an output for each colour bead/light colour combination applied.

The light sensitive elements are able to convert the light energy received into voltage which may then be converted into digital data. In this way, the surface comprising the elements is itself capable of detecting the presence of a molecule by detecting a bead attached to that molecule. There is no need for external expensive equipment to be employed to detect the presence of the signal or label attached to the molecule. The surface itself is able to detect the molecule.

As noted above, known CMOS or CCD detectors are suitable for detecting the beads. For example, image chips of the sort used in mobile phones can be used for detecting beads in the method of the invention. Hence the surface of, for example a CMOS or CCD image sensor may form the surface used in the detection step of the invention.

The CMOS photodetector (or Active Pixel Sensor) has been developed essentially for consumer camera applications e.g. in webcams or mobile phones. Two variants of this detector are available, namely the bare die variant or a variant with the die packaged with a protective glass and bonded to pads that are connected to the external pads made for soldering. The bare die variant may be used directly in the present invention, whereas the packaged die variant CMOS photodetector may be modified by removing the glass lid. For both variants, it may be preferable to remove the layers of microlenses and colour filters which usually cover the pixels because the surface under the lenses and filters is usually a layer of glass, which is preferable, especially to avoid unspecific connection of beads. CMOS or other photodetectors may be manufactured without the additional microlens/filter layers present which are required for use in mobile phones, for direct use in the present invention. Hence, particularly adapted CMOS image chips may be used in the invention.

Particularly, the surface may comprise at least 3 Megapixels (2048×1536 light sensitive elements) or at least 4, 5, 6, 7, 8, 9, 10, 11 or 12 Mpixels. Using standard deposition processes, it may be possible to deposit polynucleotides associated with at least 1, 5, 10, 15, 20, 25, 30, 35 or 37% of the light sensitive elements. The light sensitive elements or pixels present on an image chip are usually the same size, although differences in size may occur. The pixels may be for example in the range of 0.5×0.5 µm to 10×10 µm, for example 1×1 µm, 2×2 µm, 3×3 µm, 4×4 µm, 5×5 µm or 6×6 µm and particularly, the pixels may be 1.75×1.75 µm or 3.2×3.2 µm.

Modifications may additionally be made to the surface e.g. to that of the image chips to assist in the attachment of molecules to the surface. Particularly, the image chips may be coated with gold or may be modified to have silane or antidigoxigenin groups attached. The thickness of the layer of gold which may be used is not critical provided that too much light is not blocked from reaching the light sensitive elements. For example, gold layers may range from 5 to 50 nm. Methods of modifying surfaces in such ways are known in the art. Gold coating may be carried out by vacuum deposition or by deposition from a highly concentrated gold solution. Aminosilane modification of surfaces can be achieved by for example incubating the surface with 5% aminopropyltriethoxysilane (CAS:019-30-2) in dry acetone for one hour at room temperature. Aminosilane surfaces can be used as is, to add desired molecules directly, or can be further modified by adding a bifunctional crosslinker, such as m-maleididibenzoyl-N-hydroxysulfo-succinimide ester in order to be able to bind molecules to the surface. Antidigoxigenin modification is achieved by first priming the surface with a poly-1 lysine solution (10% poly-1 lysine v/v and 10% PBS), and then by adding antidigoxigenin 1:100 in Invitrogen CNB0011 coating buffer A.

Additionally, the surface may be equipped with a flow cell which allows fluid flow to and from the surface. Hence, the flow cell can be used to apply beads or bead labelled bases/probes or unlabelled bases/probes. Further, the surface may be arranged with a reader which is capable of detecting and reading the signals from each of the sensory elements in or on the surface. The output from each element may be received by a computer. A flow cell may easily be made to contain more than one chip, e.g. it may be produced with 64 image chips. In that case all the chips may be controlled from the same control unit.

The shape of the surface may be additionally or alternatively modified or adapted to assist the binding of beads to the incorporated bases or probes or to assist the binding of bead labelled bases/probes at each position or pixel and to allow a sensitive and accurate method. Hence, the surface may be modified or adapted, for example shaped, to allow the binding of a bead at each position.

Therefore, the surface may be contoured to allow the association or binding of a bead with each sensory (e.g. light sensitive) element. Individual recesses may be associated with or located by each sensory element or groups of sensory elements which allow each bead to attach and to be associated with a single or individual sensory element or group of sensory elements on the surface. The recesses may allow the bead to be positioned only over a single element and to prevent movement of the bead over more than one sensory element or group of sensory elements.

Alternatively, each sensory element or group of sensory elements may be surrounded by a barrier to enable bead attachment and association with only that sensory element or group of sensory elements. Hence, barriers or obstacles may be placed on the surface around the one or more sensory elements.

A combination of recesses and barriers may also be used on a surface. Typically, the sensory elements which will have a polynucleotide attached thereto will be adapted to have a recess or barrier associated therewith. One or more elements on a surface may be adapted, although typically all of the elements may be adapted e.g. to have recesses and/or barriers associated therewith.

The adaptation of the surface in this way e.g. the use of recesses and/or barriers allows a more sensitive and accurate method and may allow longer polynucleotides to be sequenced. Thus, the surface may be adapted to allow the binding of a single bead at each position. Each sensory element or sensory element group and its surrounding barrier or recess may therefore be of a suitable size to bind an individual bead. The sensory element and/or barrier/recess may therefore be adapted to suit any particular bead size used with the surface. The surface may be adapted using techniques well known in the art.

In addition, to allow connection of target polynucleotides to sensitive areas of the detector (e.g. for light or magnetism) modifications may be necessary. This may be achieved for example by lithographic methods, e.g. defining islands of a gold layer which may connect to a thiol modification at one end of the target anchorage to the surface or by defining islands that are silanized.

Different polynucleotides may be sequenced simultaneously at different positions on the surface. To do so it will be necessary to determine their position on the surface before commencing sequencing. Alternatively, overlapping fragments of a polynucleotide may be generated and placed randomly at separate positions on the surface for sequencing. In this instance, it is not necessary to determine the positions of each fragment on the surface prior to sequencing since the overlapping sequences can be pieced together after sequencing has been completed.

By way of example, the method may be put into practice as follows. Firstly, target polynucleotide should be isolated and prepared for sequencing The target polynucleotide should then be attached to the solid support either directly or indirectly as described hereinbefore. In an aqueous reaction mix, the test complementary base and/or probes to be used in the method (which may carry the signalling means, e.g. bead) are added under conditions which allow them to bind to the target polynucleotide. Enzymes necessary for achieving covalent binding (e.g. ligases and optionally polymerases) may be added simultaneously or before or after the addition of the optionally signalling means labelled test complementary base and/or probes. Once covalent binding has been achieved, the complexes should be washed to remove unbound bases and/or probes. Following this step either signalling means detection (as described hereinbefore) may take place or the signalling means may be added to label the complex. In the latter case, signalling means carrying the relevant binding partner may be added under conditions suitable for binding to occur between the binding partners and the presence or absence of signalling means may then be determined after washing to remove unbound signalling means, e.g. beads.

If signalling means are to be detected only on their release the washing and bead binding steps may be performed without detection. Release of the beads is performed as described hereinbefore, i.e. by enzymatic cleavage, e.g. by addition of consecutive restriction enzymes. The released probe and/or bases carrying the signalling means may be removed from the reaction mix and the identity of the signalling means determined.

When more than one set of probes are used in the above steps at one time, the cycle may be completed by performing those steps only enough times such that all sets are used, for example when 16 probe sets are to be used with 4 discriminating recognition sites and cleavage enzymes, each set of steps may be performed 4 times in which the binding of 4 probe sets is assessed each time the sequence of steps is completed. Once the cycle is completed and the one or more bases to be sequenced in that cycle has/have been determined, the cycle may be repeated. Thus preferably the methods as described hereinbefore include the steps of adding the relevant enzyme, washing the complexes to remove unbound enzyme, probes, bases or beads.

The invention will now be described by way of a non-limiting Example with reference to the drawings in which:

FIG. 1 shows sequencing by stepwise ligation and cleavage using a related method to the method of the invention. Thus, a polynucleotide (DNA) whose sequence is to be determined is immobilised to a solid support where the polynucleotide has a protruding portion (AGC). Probes are produced which also have a protruding portion (on the opposite strand to the protruding portion of the polynucleotide), where the outermost base is known and the other 2 bases are degenerate. The probes are labelled with 4 different beads, representing one base each, and are added to the polynucleotide. The probe with the complementary protruding portion to the polynucleotide will be incorporated into the polynucleotide using ligase. The incorporation of the probe and thus the known base can be detected by the bead characteristics. Once the bead label has been determined, the polynucleotide/probe complex can be cleaved at the positions shown by the arrows using a nuclease. This cleaves the complex, resulting in the removal of the terminal C residues in the original polynucleotide and hence a one base shorter polynucleotide which can then be subjected to further rounds of ligation and cleavage of probes.

EXAMPLE 1

Sequencing by Sequential Ligation and Cleavage

Preparation of the Apparatus

A Micron MT9T001 (Aptina) 3 Mpixel CMOS digital image sensor is soldered onto a printed circuit board (PCB) and tested for functionality by connection to the Blackfin microcontroller from Analog Devices a microcontroller using the PPI (parallel peripheral interface).

After soldering to the PCB, the protective glass is carefully removed from the CMOS digital image sensor by a diamond cutter, and the chip surface is cleaned by washing with pure ethanol. The microlenses and Bayer filters are removed by exposing the inner chamber to acetone for 15 minutes. Thereafter the upper layer is removed by careful scraping with a plastic toothpick.

Assembly of the Flow Cell

Figure 1:
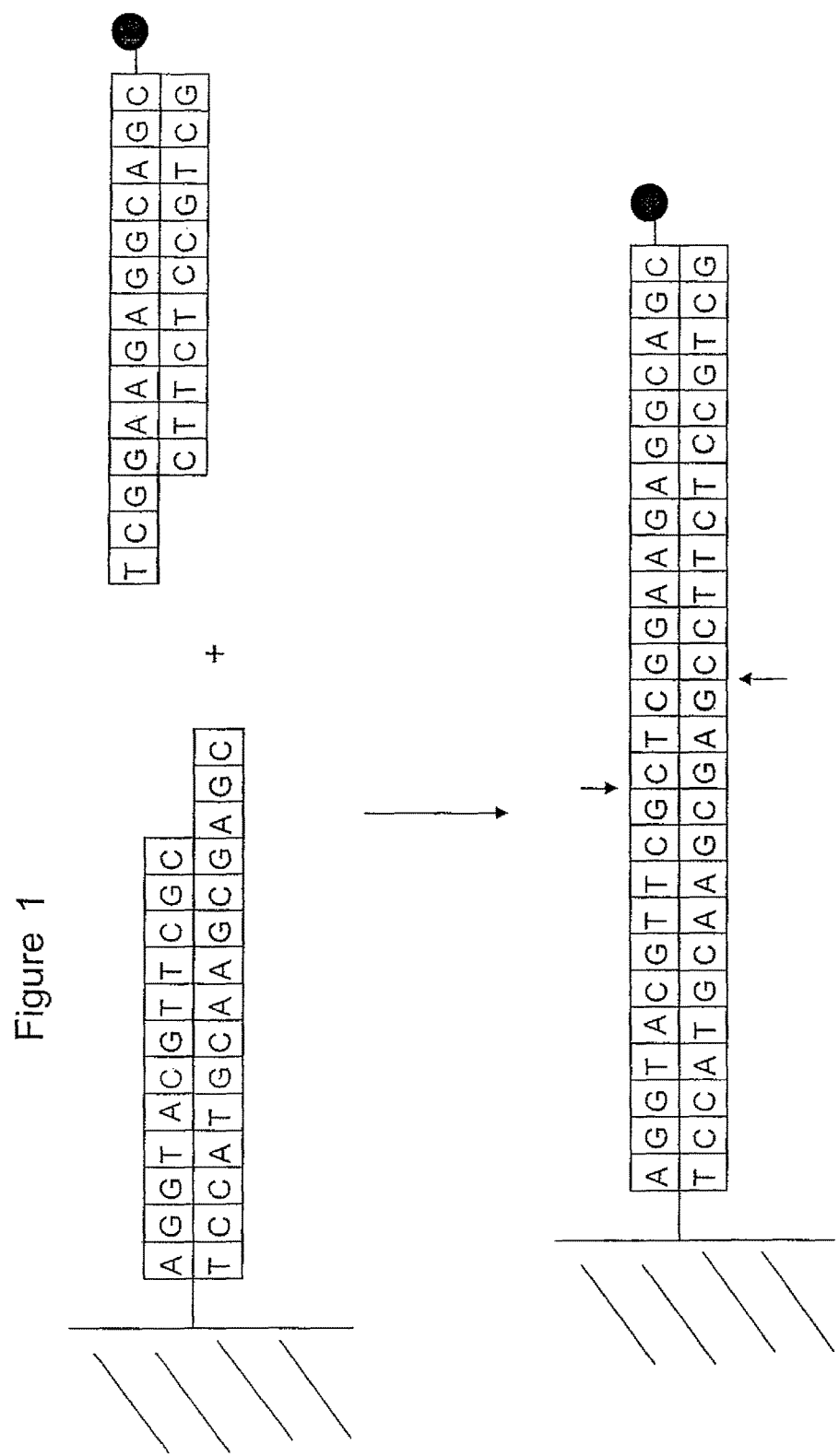
Figure 2:
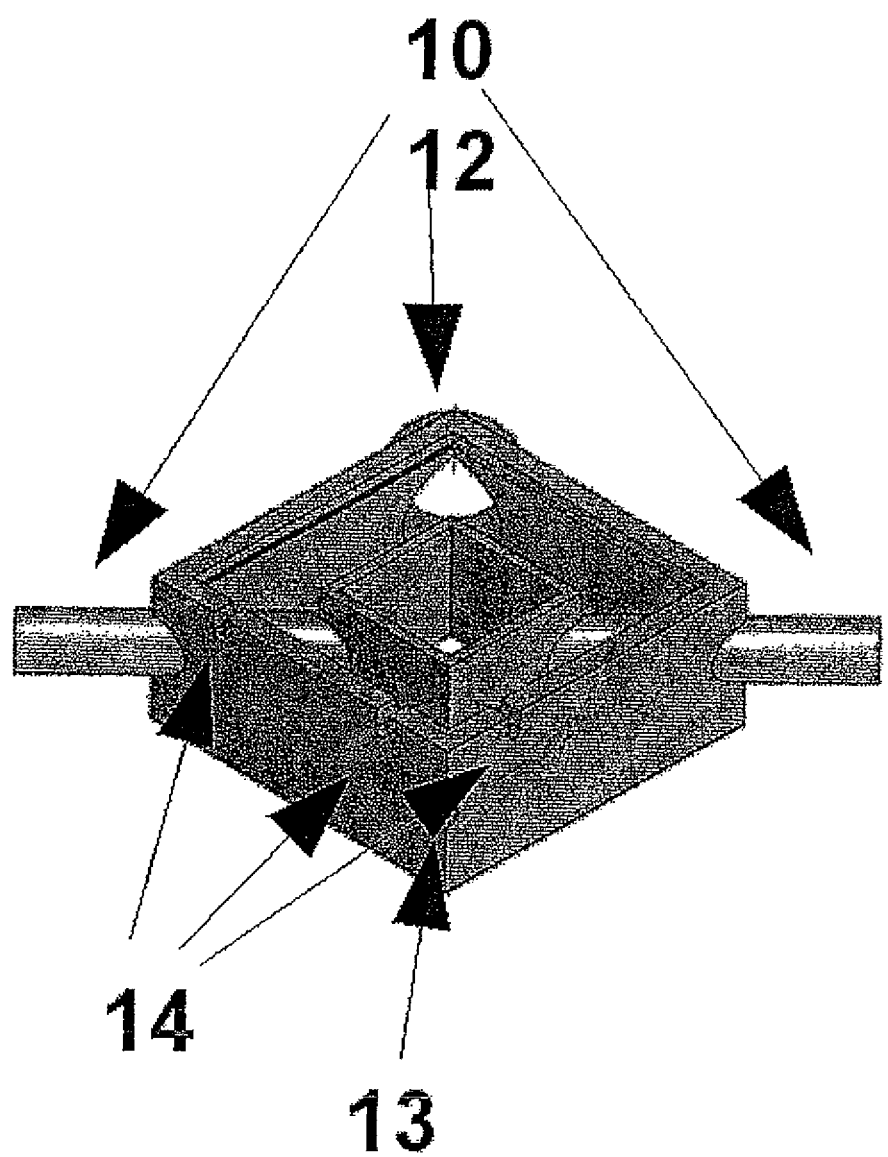
FIG. 2 shows a 3D printed unit to be placed upon a packaged image chip to produce a flow cell.

A flow-cell (FIG. 2) is produced from plastic by 3D printing so that it fits with the size of the MT9T001 CMOS digital image sensor and allows fluid flow to and from the active surface through inlet and outlet (10) which can be connected via flexible plastic tubes.

A thin layer of epoxy glue is distributed on the edge e.g. by stamping it towards a thin layer of fluid glue. It is then placed upon the chip, and the epoxy is allowed to harden. For some of the chips, microlenses and Bayer filters are removed at this stage. A resistor network together with an NTC resistor used as temperature sensor is fitted into the compartment before the cover glass is positioned. Electrical connections to the control circuitry is through connectors protruding through the cuts (14) in the flow cell.

A cover glass is placed on the top, covering both inner and outer compartments, and the outer compartment is filled up with epoxy glue through the inlet hole (12), letting air out through the outlet hole (13). The inner compartment is thereby sealed, and the outer area of the chip and all open bonding wires are protected.

Chip Device Based on a Wafer (Bare Die)

Figure 3:
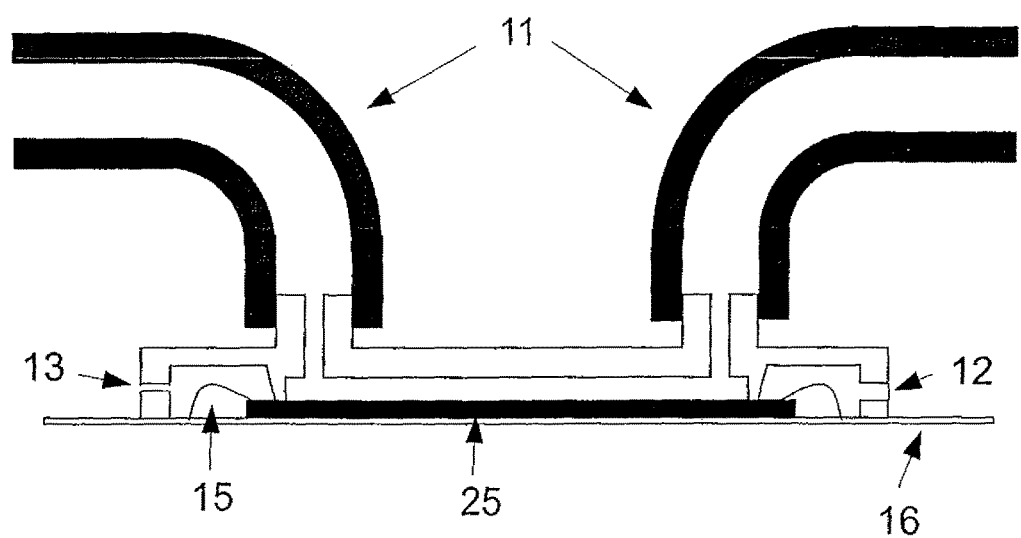
FIG. 3 shows a cross-section of a flow cell placed upon a "bare die" image chip glued and bonded to a printed circuit board.
Figure 4:
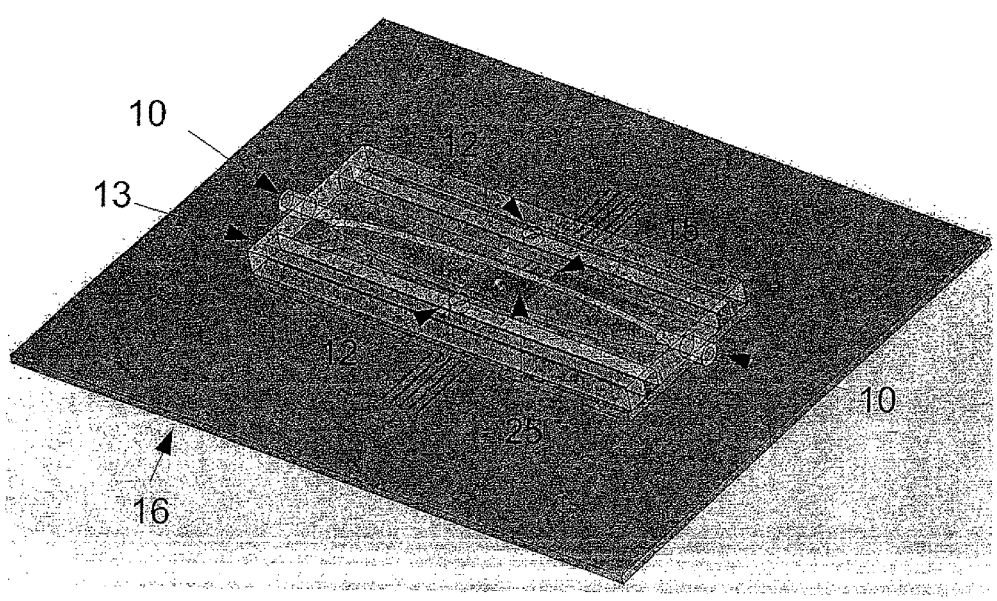
FIG. 4 shows a 3D picture of another flow cell, with better fluid flow characteristics, placed upon a "bare die" image chip glued and bonded to a printed circuit board.

The wafer is removed from the normal production line before the Bayer filters and any other filters and lenses are equipped. Alternatively these can be removed with NaOH prior to further preparation. Any preparation to enhance the polymer anchorage may now conveniently be performed, e.g. metallisation, using a mask that protects the connection islands. The wafer is tested and cut into chips in the normal way (bare die). FIGS. 3 and 4 shows a chip device. The chip (25) is connected to the board by gold wires through bonding (15). The reaction chamber unit is placed on top of the chip. It is then first glued to the chip, and the enclosed volume containing the bonding connections is filled with epoxy through the inlet (12) while air is let out at the outlet (13).

The reaction volume is connected to the fluid supply and discharge units by plastic tubes (11). This may for small series production be produced in one unit by transparent plastic 3D printing, while for larger series, it may be produced e.g. from one plastic sheet with cavities at both sides and one flat, transparent sheet. The former may be produced from a flat sheet by milling or through moulding.

Figure 5:
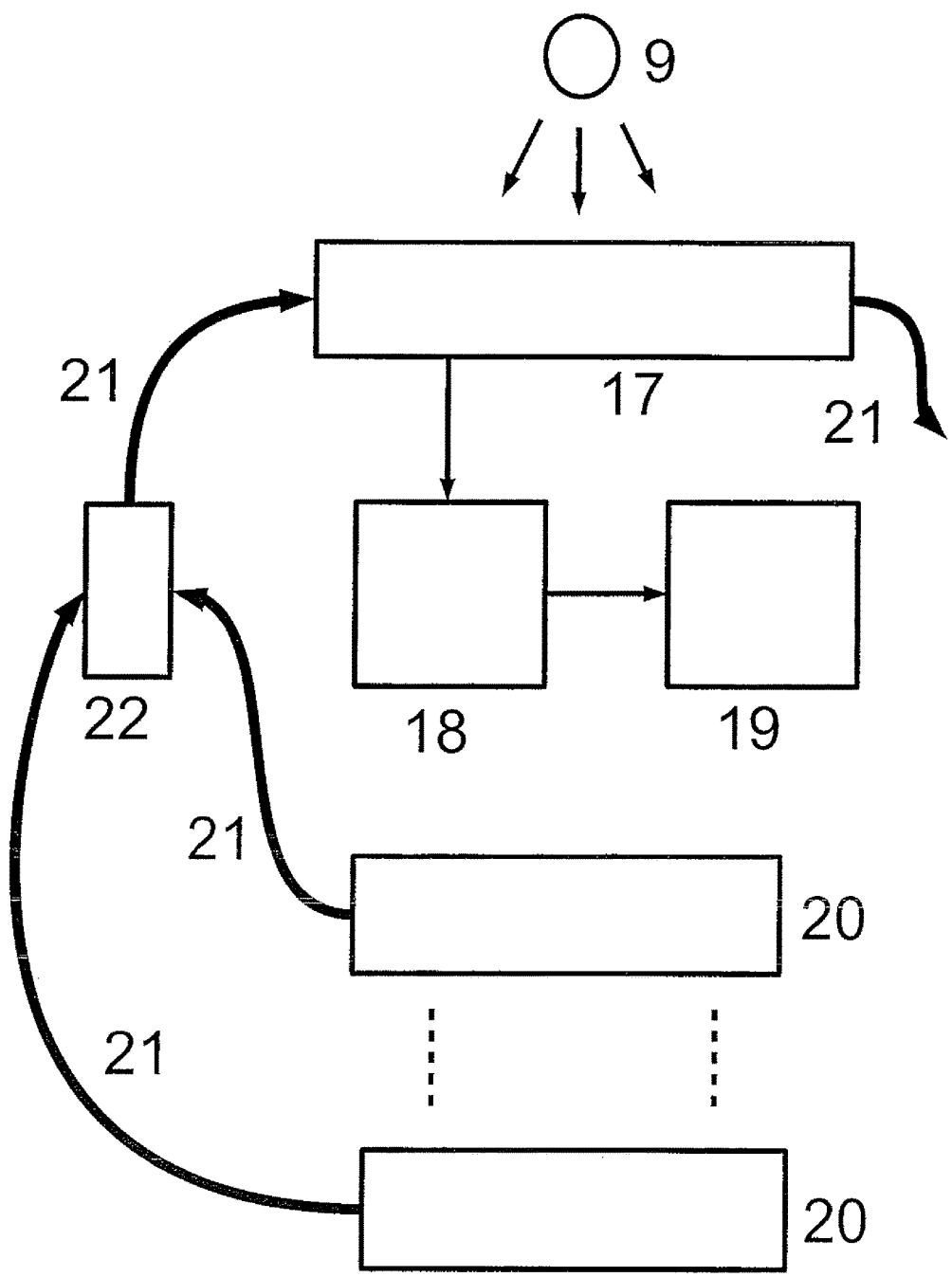
FIG. 5 shows a schematic view of the complete system of the image chip.

Connection of Imaging Device to Controlling and Image Collection Units:

The imaging device (17) is connected as shown in FIG. 5. It is possible to capture images in the Blackfin control unit (18) using hardware acceleration (direct memory access from image chip to RAM). Clock signal to the image chip could either be generated by a crystal or generated by Blackfin. By using the uClinux distribution, the test program ppifcd_test which is distributed with the package, it is possible to capture to a RAM-disk file. This is described in the uClinux wiki found at the following link: http://docs.blackfin.uclinux.org/doku.php?id=frame_capture_device. A copy of the text at this link is found as Appendix 1, but modified to remove non-functional links.

This file can then be transferred to a computer (19) over a network (if using a development board with an ethernet controller) by using NFS, tftp, ftp etc. or using USB.

Connection of Imaging Device to Fluid Supply Units:

The imaging device (17) is further connected to the fluid supply units as shown in FIG. 5. The fluid supply consists of a number of separate fluid containers (20) each equipped with its own motor controlled syringe to drive the fluid through the tubing (21) to the manifold (22) and further to the imaging device (17). Used fluid is discharged into a container.

Silanization of Image Chip:

The surface is functionalized by soaking the chip in NaOH (1 M) for 1 hour, rinsing with water and drying under a stream of nitrogen gas. To produce a negatively charged surface this procedure is repeated using HCl (1 M) instead of NaOH. For silanisation the image chip is covered in a 5% solution (volume/volume) (3-Aminopropyl)triethoxysilane (CAS: 919-30-2) in dry acetone, 1 hr RT. The image chip is then washed three times with acetone using 5 minutes incubation times. Then the chip is rinsed in ethanol and subsequently dried under $N_2$ gas. Crosslinking is performed by incubating the image chip for 5 hours in a solution of the heterobifunctional linker m-Maleimidobenzoyl-N-hydroxysulfosuccinimide ester (s-MBS) (20 mM) in PBS (0.1 M $NaH_2PO_4$, 0.15 M NaCl, (pH 7.2)). The image chip is then washed in PBS, immersed in deionized water, then in ethanol and finally dried in a nitrogen stream.

Preparation and Attachment of Anchorage DNA to Image Chip

The DNA to be sequenced is to be ligated to an anchorage DNA on the chip surface. The anchorage DNA is bound to the chip through a covalent bond. An anchorage DNA might be prepared by annealing two oligonucleotides that form a double stranded DNA molecule containing thiol in one end, and where the other end is sticky. (It might also be formed by PCR-amplification of a part of a suitable plasmid where one of the primers is 5'-thiolated. The sticky end will then be obtained using a restriction enzyme.) To activate the 5' thiol, the disulfide linkage (S—S) needs to be reduced into free thiol (H—S). This is achieved by incubating the prepared anchorage DNA for 2 hours in the reducing agent Tris(2-carboxyethyl)phosphine hydrochloride (TCEP) (10 mM) in Tris-HCl (0.1 M, pH 7.5). The anchorage DNA is then purified by a Biospin30 column (Bio-Rad) according to instruction manual by eluting DNA with NaPi buffer ($NaH_2PO_4$ (0.1 M, pH 6.5), NaCl (0.15 M)). Then the anchorage DNA is diluted in NaPi buffer to a final concentration of 0.01 µM. The reduced and purified anchorage DNA is immediately applied to the image chip and incubated for 5 hours in a humid environment. The image chip is then flushed with NaPi, blocked for 1 h in Mercaptoethanol (10 mM) in NaPi, and again rinsed with NaPi. It is then flushed with a solution of NaCl (1.5 M) in $NaH_2PO_4$ (10 mM, pH 7.0), and incubated with this solution for five minutes to eliminate non-specific attachment of polynucleotides to the chip surface. Thereafter it is flushed with 5×SSC (0.075 M sodium citrate, 0.75 M NaCl (pH 7.0)) with 0.1% Tween20, with just 5×SSC, and stored in 5×SSC at 4° C. until further use.

Sequencing by Sequential Ligation and Cutting

Beads: Streptavidin coated 2.8 µm Øparamagnetic beads.

Probes: Four different mixes of probes, consisting of 34 base pairs with a 5' end protruding 3 base overhang at one end and multiple biotins at the other end. One base is held constant in each probe mix (A, C, G, and T), the other bases in the overhang are totally varied. The base chosen to be fixed is the one closest to the ligation point. The 5' ends of the probes does not contain phosphate to avoid ligation between two probes.

Preparation of Targets and Beads for Sequencing:

To ensure that the recognition sequence of the restriction enzyme used in the sequencing reaction (Earl in FIG. 6) is not present in the DNA to be sequenced, a cleaving step with the enzyme is performed. Then the DNA is sheared into fragments in a nebulizer or a HydroShear device set to an average length of 3000 base pairs. The size distribution may be narrowed by separating the DNA on an agarose gel followed by purification of the fragments of the wanted length. Single stranded nicks in the DNA obtained during the shearing process is repaired using T4 DNA ligase. A DNA polymerase is used to fill in or remove the overhangs (e.g. DNA polymerase I, Large (Klenow) fragment).

Figure 6:
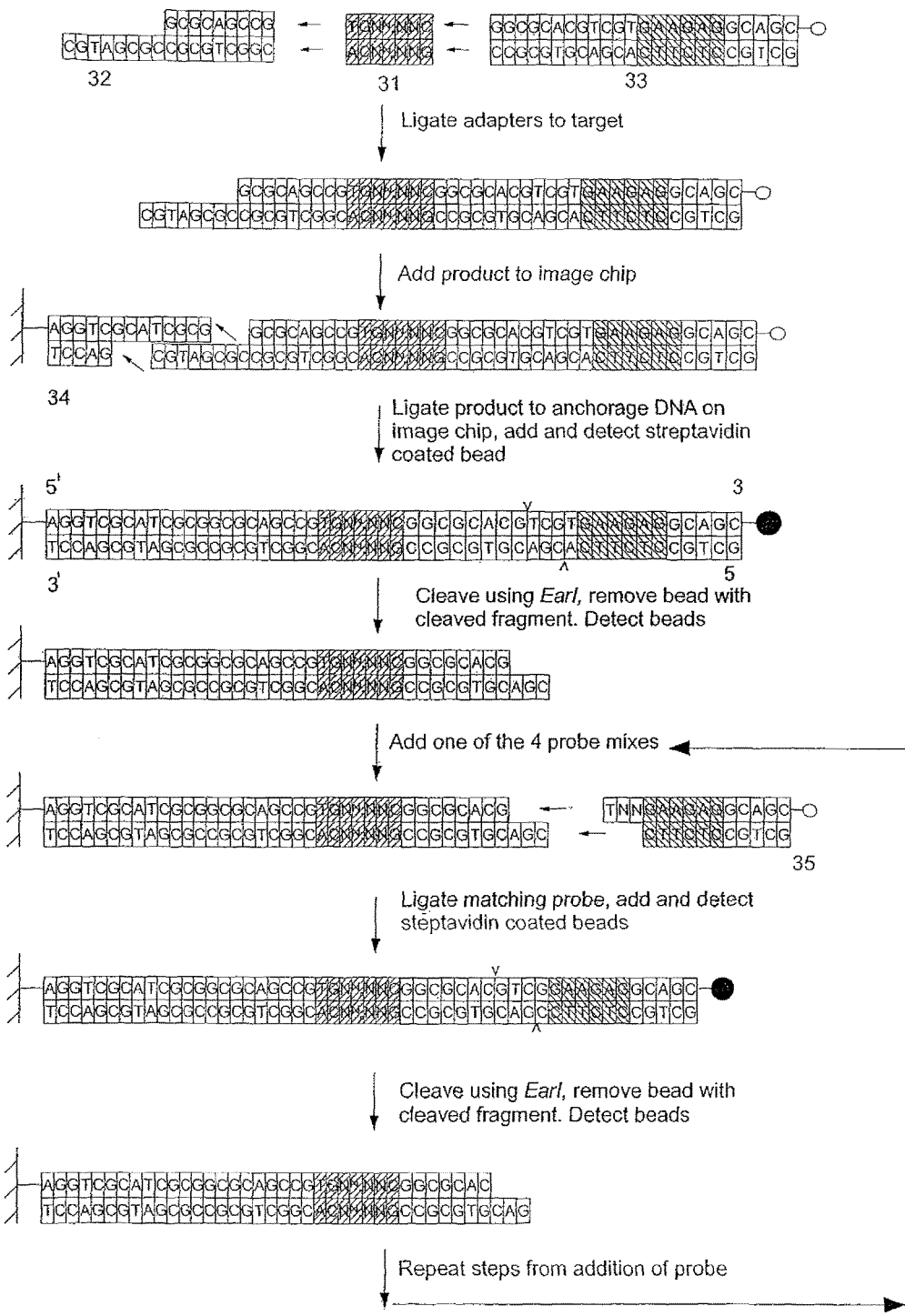
FIG. 6 shows the sequencing procedure described in Example 1.

The target is illustrated as the fragment marked 31 in FIG. 6. The adapter 32 is the anchorage adapter. Adapter 33 is needed for subsequent ligation to the sequencing probe in the first sequencing step. If these adapters are of approx. the same length, they are supplied in the same amount. Adapter 32 contains a region which is complementary to the sticky ends of the anchorage DNA on the solid support, and hence can be ligated to these. Adapter 33 contains the restriction site (hatched area) used to remove the beads connected to biotin (open circle) and is long enough to allow enzymes to operate close to the bead.

The beads are prepared as described in the product guide from Dynal using the procedure "Immobilization of nucleic acids"

The Further Procedure is as Follows, with Reference to FIG. 6.

Ligate adapters to target: The two adapters (32 and 33) are ligated to target DNA by a 2-step ligation. First, one adapter is supplied in excess, together with 400 cohesive units (U) of T4 DNA ligase. Ligation takes place at 25° C. for 2 hours. The ligation products are then purified using PCR-purification, which will remove the non-ligated adapter fragments due to their small size. After purification, the other adapter is supplied in excess, together with 400 cohesive units (U) T4 DNA ligase. In addition to the wanted product 32-31-33, the products 32-31-32, 33-31-33 and some self-ligated target DNA will appear. The 32-31-32 and the 33-31-33 products are not detrimental in the method, as they will associate only with the image chip or with the bead, respectively. The self-ligated target DNA will not associate with chip or bead.

If, however, the two adapters linked together (32-33) are small enough to be removed by PCR-purification, only 1 ligation is necessary, and is carried out by adding both adapters in excess in a proportion that makes them ligate to 31 with the same probability as described below.

The two adapters are supplied in excess, together with 400 cohesive units (U) T4 DNA ligase, in a proportion that makes them ligate to 31 with the same probability. Ligation takes place at 25° C. for 2 hours. In addition to the wanted product 32-31-33, a lot of 32-33 ligation products (the two adapters ligated together), the products 32-31-32 and 33-31-33 appear, together with self-ligated target DNA. The product 32-33 and self-ligated target DNA are removed by separation on an agarose gel followed by DNA purification. The 32-31-32 and the 33-31-33 products are not detrimental in the method, as discussed above.

Add product to image chip: A small part of the resulting product mixture is added to the assembled flow cell together with 400 U of T4 DNA ligase.

Ligate product to anchorage DNA on image chip: 32-31-33 products are ligated to the sticky ends of the anchorage DNA (34 in FIG. 6) that are prepared in excess in the pixel windows. Ligation takes place at 25° C. for 10 minutes. Afterwards the non-reacted molecules and enzymes are washed away with buffer suitable for bead binding.

Add and detect streptavidin coated beads: Approx $2 \times 10^6$ beads are added and incubated for 30 minutes. The assembled flow cell is gently shaken for 5 seconds each minute. All unbound beads are removed by careful washing. An image of the beads is registered while an upward magnetic field is applied to stabilize the beads Check bead density: The image is inspected to see that between 5 and 10% of the pixels have a bead positioned to give a shadow on primarily one pixel. If too few beads are present, the procedure is repeated from "Add product to image chip".

Cleave using Earl, remove beads with cleaved fragment: Washing is performed with restriction enzyme buffer and then 1 U of nuclease Fast Digest (FD) Earl (Fermentas) is added in its reaction buffer and cleaving occurs in 5 minutes at 37° C. The nuclease and the beads connected to the released fragments are washed away with buffer appropriate for T4 DNA ligase. An image of the remaining beads is registered while an upward magnetic field is applied.

This method may also be performed in which a different restriction enzyme specific for the adapter is used. In this case washing is performed with restriction enzyme buffer and then an appropriate amount of restriction enzyme is added in its reaction buffer and cleaving occurs until most probes have been cut. The nuclease and the beads connected to the released fragments are washed as above. An image of the remaining beads is registered as above.

Sequencing by Sequential Ligation and Cutting

Add one of the 4 probe mixes: Probes of type A (35) are added together with 400 U of T4 DNA ligase and its reaction buffer.

Ligate matching probe: The matching probe is allowed to anneal and ligate to the cleaved fragment during an incubation at 25° C. for 10 minutes. The ligase together with unbound probes are washed away with reaction buffer suitable for bead binding.

Add and detect streptavidin coated beads: Beads are added and an image is registered as explained above.

Release sequencing beads, register for verification: The procedure described earlier as "Cleave using Earl, remove beads with cleaved fragment" is followed.

The steps are repeated, each time adding a different (C, G or T, and then A again) probe type. This is performed repeatedly, until the number of beads registered in each cycle is drastically reduced or the anchor sequence is read in most of the pixels, indicating that most of the target reading has been completed.

Figure 7:
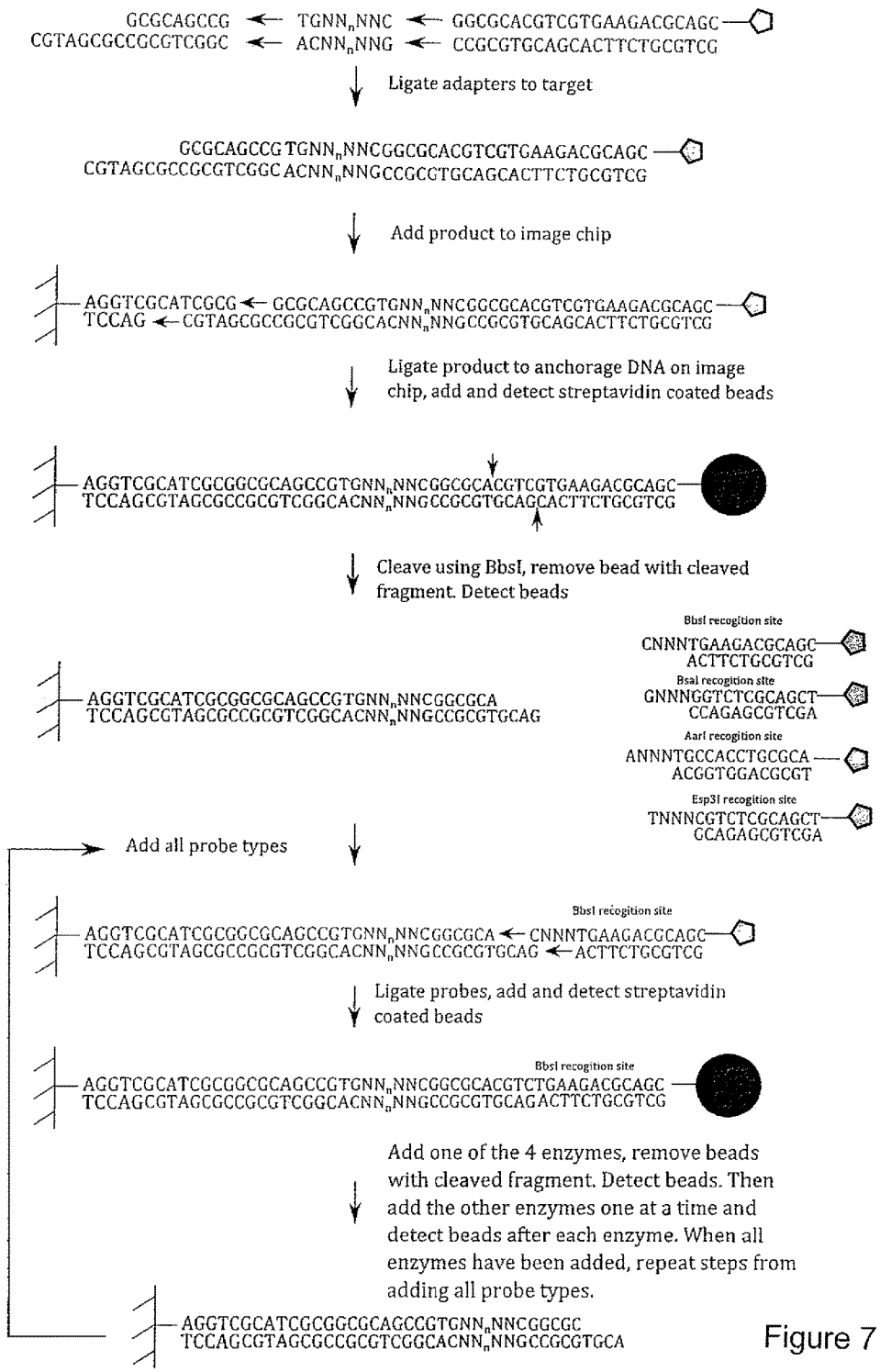
FIG. 7 shows the sequencing procedure described in Example 1 in which multiple cleavage enzymes are used.

The sequencing method according to the invention in which multiple cleavage enzymes are used during the stepwise ligation and cleavage method is performed as follows. The protocol which is used is illustrated in FIG. 7.

Four different mixes of probes are used as described above in which each probe mix has a restriction site for a different restriction enzyme. The adapter (33) has one of these restriction sites. The method proceeds as follows:

Sequencing by Sequential Ligation and Cutting

Add one of the 4 probe mixes: Probes are added together with 400 U of T4 DNA ligase and its reaction buffer.

Ligate matching probe: The matching probe is allowed to anneal and ligate to the cleaved fragment during an incubation at 25° C. for 10 minutes. The ligase together with unbound probes are washed away with reaction buffer suitable for bead binding.

Add and detect streptavidin coated beads: Beads are added and an image is registered as explained above.

Release sequencing beads: Restriction enzyme recognizing of the 4 probe mixes is added. After the enzyme reaction is completed, the enzyme and released probe is washed away, and an image of the remaining beads is registered while an upward magnetic field is applied. Then, this step is repeated by adding restriction enzymes that recognize probe mix 2, 3 and 4 respectively, one by one.

The steps are repeated from addition of probe mix until the number of beads registered in each cycle is drastically reduced or the anchor sequence is read in most of the pixels, indicating that most of the target reading has been completed.

EXAMPLE 2

Procedure for Surface Modification of Image Chip by Silanisation Using APTES and Crosslinking with Glutaraldehyde This procedure is an alternative way of silanising the chip surface. The procedure is a modification of those of Howarter et al (2006, Langmuir, 22, p 11142-11147), Aksyonov et al (Anal. Biochem., 2006, 348, p 127-138), and Wang et al (J. Agric. Food Chem., 2007, 55, p 10509-10516). DNA with 5'-amine groups can bind to the aldehyde groups of the cross linker, and the amine group can be made a part of the anchorage DNA in the same way as the 5'-thiol group was attached to the anchorage DNA in Example 1.

1. Soak the chip in a solution of 1 M NaOH for 1 hour.
2. Rinse the chip thoroughly with deionized water and dry under a stream of nitrogen.
3. Treat the chip with 1 M HCl solution for 1 h to create a negatively charged surface.
4. Rinse the chip thoroughly with deionized water and dry under a stream of nitrogen
5. Move the chip to a glove box, with humidity and oxygen levels at 0.1 ppm Treat the chip with a solution of 5% (3-Aminopropyl)triethoxysilane (APTES) in anhydrous toluene for 1 h.
6. Rinse with anhydrous toluene.
7. Move the chip to normal atmosphere, and rinse with methanol and thereafter with deionized water. Incubate in deionized water for 24 hours in order to fully hydrolyze the APTES molecules on the chip.
8. Dry the chip under nitrogen.
9. Bake at ~120° C. for 1 h.
10. For crosslinking: Immerse the chip in 5% glutaraldehyde in a 10× phosphate-buffered saline (PBS) solution overnight.
11. Wash with deionized water and dry under a stream of nitrogen.
12. After being dried, the aldehyde-modified glass slides can be stored in a dark place at 4° C.

Appendix 1

PPI Frame Capture Device

The PPI frame capture device (PPIFCD) is a CMOS camera that connects to a Blackfin via the parallel peripheral interface. It is intended to only capture single frames. Currently two camera sensors are supported.

See here: v4l_blackfin_camera for an v4l video driver supporting several sensors.

Micron MT9T001

The PPIFCD can be built using a Micron MT9T001. It uses the standard Inter-IC Bus and the programmable flags to control the camera (e.g., to take out of standby mode, etc.).

Programs that Use the PPIFCD ppifcd_test

The PPIFCD Frame Capture Driver test application aims to see if the digital image sensor can take pictures effectively which is connected through the PPI port to the target board.

It records the row time, total_frame_time, total_frame_capture_time, and the taken picture. If the printed data is as expected, the case passes, otherwise it fails.
fcd
This program serves CGI-based web pages that allow the user to specify settings, capture frames, and verify the overall operation of the camera.
Configuring the uClinux Kernel
The Blackfin PPI supports a number of daughter cards, the PPIFCD being one. However, the PPI Driver will conflict with the PPI Camera frame capture driver if both are enabled. You will see this in the kernel log (i.e., dmesg) when the PPI drivers try to register the same major number for the char device.
Below are some configuration settings for the BF533 and BF537 STAMP boards. To get either of the programs mentioned above built, specify the following:
under Customize Vendor/User Settings
==Select Blackfin test programs==
Enable PPIFCD test program
==Select Blackfin app programs==
Enable CGI based Test Application for the PPI Frame Capture Driver
BF533-STAMP Board
As described here, the BF533-STAMP board is known to work with the PPIFCD with the following settings:
under Customize Kernel Settings
==Select Device Drivers==
==Select Character devices==
Enable [*] Blackfin BF53x Programmable Flags Driver
Enable [*] Blackfin BF5xx PPI Camera frame capture driver
[ ] Blackfin BF5xx PPI Driver
==Select I2C support==
Enable I2C support
Enable I2C device interface
Select I2C Hardware Bus support
Enable Generic Blackfin and HHBF533/561 development board I2C support
Select BFIN I2C SDA/SCL Selection
set (2) SDA is PF[0:15]
set (1) SCL is PF[0:15]
BF537-STAMP Board
The BF537 has a built-in two wire interface peripheral and unlike the BF333 does not require the generic I2C support.
under Customize Kernel Settings
==Select Device Drivers==
==Select Character devices==
Enable [*] Blackfin BF53x Programmable Flags Driver
Enable [*] Blackfin BF5xx PPI Camera frame capture driver
[ ] Blackfin BF5xx PPI Driver
==Select I2C support==
Enable I2C support
Enable I2C device interface
Select I2C Hardware Bus support
Enable Blackfin TWI I2C support

The invention claimed is:

1. A method for determining a nucleotide sequence of a polynucleotide, preferably immobilised on a solid support, comprising the steps of:
   (i) contacting said polynucleotide with a) at least a first and second test probe each comprising a portion which may be complementary to one or more bases in said polynucleotide, and optionally, in addition, b) at least one test complementary base each of which may be complementary to a base in said polynucleotide, and covalently binding said first or second test probe to said polynucleotide when said portion of said first or second test probe is complementary to said one or more bases in said polynucleotide by ligation of said first or second test probe to said polynucleotide;
   (ii) adding a first enzyme capable of removing at least part of said first test probe and at least one base of the polynucleotide being sequenced by a cleavage reaction if said first test probe bound to said polynucleotide and then sequentially adding at least a second enzyme capable of removing at least part of said second test probe if said second test probe bound to said polynucleotide, wherein each of said enzymes is different and specific for said first or second test probe;
   (iii) optionally repeating steps (i) and (ii) with at least two different test probes and at least two enzymes wherein said enzymes may be the same or different to the enzymes used in step (ii) until a test probe which has a portion which is complementary to said one or more bases has bound to said polynucleotide and optionally, in addition, a test complementary base has bound to said polynucleotide, wherein only one test probe used in step (i) or step (iii) has a portion which is complementary to said one or more bases in said polynucleotide and optionally, in addition, only one test complementary base used in step (i) or step (iii) is complementary to a base in said polynucleotide, and said only one test probe binds to said polynucleotide in step (i) or step (iii) and optionally, in addition, said only one test complementary base binds to said polynucleotide in step (i) or (iii);
   (iv) determining which test complementary base and/or complementary portion of the test probe bound to said one or more bases of the polynucleotide by determining whether said test complementary base and/or test probe bound to said polynucleotide during steps (i), (ii) or (iii) to thereby identify said one or more bases of the polynucleotide;
   wherein each cycle of steps (i) to (iv) is performed one or more times, and in each cycle one or more bases of said sequence are identified, and wherein determining step (iv) comprises determining the presence, absence or level of a signal associated with said test probe and/or test complementary base, wherein the presence of signal is indicative of binding of said test complementary base and/or test probe and said signal is provided by a label associated with said test probe and/or test complementary base, and wherein said label is a bead and wherein the same bead is used for each test probe and/or test complementary base and said label is used to identify the one or more bases which are identified by determining which test probe is cleaved during step (ii).

2. The method as claimed in claim 1 wherein in step (i) at least a first, second, third and fourth test probe each comprising a portion which may be complementary to one or more bases in said polynucleotide is used and in step (ii) at least a first, second, third and fourth enzyme is used.

3. The method as claimed in claim 2 wherein in each cycle one base is identified.

4. The method as claimed in claim 1 wherein in step (i) at least a first and second test probe each comprising a portion which may be complementary to one or more bases in said polynucleotide is used and in step (ii) at least a first and second enzyme is used and in each cycle more than one base of said sequence is identified.

5. The method as claimed in claim 1 wherein at least two cycles are performed.

6. The method as claimed in claim 1 wherein said enzyme is a nuclease which has a cleavage site separate from its recognition site and said test probe contains a recognition site for said nuclease and each enzyme used in said method has a different recognition site.

7. The method as claimed in claim 6 wherein said enzyme is a restriction enzyme, preferably a type IIb restriction enzyme and each enzyme used in said method is a different restriction enzyme.

8. The method as claimed in claim 1 wherein the level of signal associated with said test probe and/or test complementary base before and after said cleavage step is determined and a decrease of signal after cleavage is indicative that said test complementary base and/or test probe bound to said polynucleotide.

9. The method as claimed in claim 1 wherein said label is attached to said test probe and/or test complementary base.

10. The method as claimed in claim 9 wherein a first binding partner of a binding pair is attached to said test probe and/or test complementary base and said label is attached to a second binding partner of said binding pair and said first binding partner is attached to said second binding partner during said method.

11. The method as claimed in claim 1 wherein the radius of said bead is larger than the length of the polynucleotide.

12. The method as claimed in claim 1 wherein said test probes comprise a recognition site for a restriction enzyme, or wherein said label and said test probe and/or test complementary base are attached through a linkage and said linkage comprises a recognition site for a restriction enzyme, and said enzyme is an enzyme used in said method.

13. The method as claimed in claim 1 wherein the bead is magnetic.

14. The method as claimed in claim 1 wherein the test complementary base or test probe is terminating on the binding of further test complementary bases or test probes.

15. The method as claimed in claim 1 wherein said label is attached to said test complementary base and/or said test probe before or after binding of the test complementary base and/or test probe to the polynucleotide.

16. The method as claimed in claim 1 wherein said first and second test probes comprise a first and second set of test probes and different labels are attached to at least two test probes of each set of test probes and/or test complementary bases and the signal associated with said different labels is detected to determine which test complementary base and/or test probe bound to said polynucleotide to determine the sequence of one or more bases of said polynucleotide, wherein the one or more bases which are identified are different to the one or more bases which are identified by determining which test probe is cleaved during step (ii).

17. The method as claimed in claim 1 wherein said label is detected using an apparatus comprising a surface provided with a means for detecting said label.

18. The method as claimed in claim 17 wherein said surface is provided with one or more sensory elements, preferably light sensitive elements.

19. The method as claimed in claim 1 wherein said determining the presence, absence or level of a signal is by detecting light changes resulting from the presence of the label on a light sensitive surface.

20. The method as claimed in claim 1 wherein said bead is removed and/or detected by its magnetism.

21. The method as claimed in claim 1 wherein said solid support is a chip.

22. The method as claimed in claim 1, wherein said bead is tethered.

23. The method as claimed in claim 22, wherein said bead is tethered to said solid support.

* * * * *

SEQUENCE LISTING

<160> NUMBER OF SEQ ID NOS: 33

<210> SEQ ID NO 1
<211> LENGTH: 12
<212> TYPE: DNA
<213> ORGANISM: Artificial Sequence
<220> FEATURE:
<223> OTHER INFORMATION: chemically-synthesized oligonucleotide

<400> SEQUENCE: 1
aggtacgttc gc                                                         12

<210> SEQ ID NO 2
<211> LENGTH: 15
<212> TYPE: DNA
<213> ORGANISM: Artificial Sequence
<220> FEATURE:
<223> OTHER INFORMATION: chemically-synthesized oligonucleotide

<400> SEQUENCE: 2
tccatgcaag cgagc                                                      15

<210> SEQ ID NO 3
<211> LENGTH: 14
<212> TYPE: DNA
<213> ORGANISM: Artificial Sequence
<220> FEATURE:
<223> OTHER INFORMATION: chemically-synthesized oligonucleotide

<400> SEQUENCE: 3
tcggaagagg cagc                                                       14

<210> SEQ ID NO 4
<211> LENGTH: 11
<212> TYPE: DNA

```
<213> ORGANISM: Artificial Sequence
<220> FEATURE:
<223> OTHER INFORMATION: chemically-synthesized oligonucleotide

<400> SEQUENCE: 4
cttctccgtc g                                                              11

<210> SEQ ID NO 5
<211> LENGTH: 26
<212> TYPE: DNA
<213> ORGANISM: Artificial Sequence
<220> FEATURE:
<223> OTHER INFORMATION: chemically-synthesized oligonucleotide

<400> SEQUENCE: 5
aggtacgttc gctcggaaga ggcagc                                              26

<210> SEQ ID NO 6
<211> LENGTH: 26
<212> TYPE: DNA
<213> ORGANISM: Artificial Sequence
<220> FEATURE:
<223> OTHER INFORMATION: chemically-synthesized oligonucleotide

<400> SEQUENCE: 6
tccatgcaag cgagccttct ccgtcg                                              26

<210> SEQ ID NO 7
<211> LENGTH: 17
<212> TYPE: DNA
<213> ORGANISM: Artificial Sequence
<220> FEATURE:
<223> OTHER INFORMATION: chemically-synthesized oligonucleotide

<400> SEQUENCE: 7
cgtagcgccg cgtcggc                                                        17

<210> SEQ ID NO 8
<211> LENGTH: 23
<212> TYPE: DNA
<213> ORGANISM: Artificial Sequence
<220> FEATURE:
<223> OTHER INFORMATION: chemically-synthesized oligonucleotide

<400> SEQUENCE: 8
ggcgcacgtc gtgaagasgc agc                                                 23

<210> SEQ ID NO 9
<211> LENGTH: 23
<212> TYPE: DNA
<213> ORGANISM: Artificial Sequence
<220> FEATURE:
<223> OTHER INFORMATION: chemically-synthesized oligonucleotide

<400> SEQUENCE: 9
ccgcgtgcag cacttctscg tcg                                                 23

<210> SEQ ID NO 10
<211> LENGTH: 39
<212> TYPE: DNA
<213> ORGANISM: Artificial Sequence
<220> FEATURE:
<223> OTHER INFORMATION: chemically-synthesized oligonucleotide
<220> FEATURE:
<221> NAME/KEY: misc_feature
<222> LOCATION: (12)..(15)
<223> OTHER INFORMATION: n is a, c, g, or t
```

<400> SEQUENCE: 10
gcgcagccgt gnnnncggcg cacgtcgtga agasgcagc                                39

<210> SEQ ID NO 11
<211> LENGTH: 47
<212> TYPE: DNA
<213> ORGANISM: Artificial Sequence
<220> FEATURE:
<223> OTHER INFORMATION: chemically-synthesized oligonucleotide
<220> FEATURE:
<221> NAME/KEY: misc_feature
<222> LOCATION: (20)..(23)
<223> OTHER INFORMATION: n is a, c, g, or t

<400> SEQUENCE: 11
cgtagcgccg cgtcggcacn nnngccgcgt gcagcacttc tscgtcg                       47

<210> SEQ ID NO 12
<211> LENGTH: 13
<212> TYPE: DNA
<213> ORGANISM: Artificial Sequence
<220> FEATURE:
<223> OTHER INFORMATION: chemically-synthesized oligonucleotide

<400> SEQUENCE: 12
aggtcgcatc gcg                                                            13

<210> SEQ ID NO 13
<211> LENGTH: 52
<212> TYPE: DNA
<213> ORGANISM: Artificial Sequence
<220> FEATURE:
<223> OTHER INFORMATION: chemically-synthesized oligonucleotide
<220> FEATURE:
<221> NAME/KEY: misc_feature
<222> LOCATION: (25)..(28)
<223> OTHER INFORMATION: n is a, c, g, or t

<400> SEQUENCE: 13
aggtcgcatc gcggcgcagc cgtgnnnncg gcgcacgtcg tgaagasgca gc                 52

<210> SEQ ID NO 14
<211> LENGTH: 52
<212> TYPE: DNA
<213> ORGANISM: Artificial Sequence
<220> FEATURE:
<223> OTHER INFORMATION: chemically-synthesized oligonucleotide
<220> FEATURE:
<221> NAME/KEY: misc_feature
<222> LOCATION: (25)..(28)
<223> OTHER INFORMATION: n is a, c, g, or t

<400> SEQUENCE: 14
tccagcgtag cgccgcgtcg gcacnnnngc cgcgtgcagc acttctscgt cg                 52

<210> SEQ ID NO 15
<211> LENGTH: 37
<212> TYPE: DNA
<213> ORGANISM: Artificial Sequence
<220> FEATURE:
<223> OTHER INFORMATION: chemically-synthesized oligonucleotide
<220> FEATURE:
<221> NAME/KEY: misc_feature
<222> LOCATION: (25)..(28)
<223> OTHER INFORMATION: n is a, c, g, or t

<400> SEQUENCE: 15
aggtcgcatc gcggcgcagc cgtgnnnncg gcgcacg    37

<210> SEQ ID NO 16
<211> LENGTH: 40
<212> TYPE: DNA
<213> ORGANISM: Artificial Sequence
<220> FEATURE:
<223> OTHER INFORMATION: chemically-synthesized oligonucleotide
<220> FEATURE:
<221> NAME/KEY: misc_feature
<222> LOCATION: (25)..(28)
<223> OTHER INFORMATION: n is a, c, g, or t

<400> SEQUENCE: 16
tccagcgtag cgccgcgtcg gcacnnnngc cgcgtgcagc    40

<210> SEQ ID NO 17
<211> LENGTH: 14
<212> TYPE: DNA
<213> ORGANISM: Artificial Sequence
<220> FEATURE:
<223> OTHER INFORMATION: chemically-synthesized oligonucleotide
<220> FEATURE:
<221> NAME/KEY: misc_feature
<222> LOCATION: (2)..(3)
<223> OTHER INFORMATION: n is a, c, g, or t

<400> SEQUENCE: 17
tnngaagagg cagc    14

<210> SEQ ID NO 18
<211> LENGTH: 11
<212> TYPE: DNA
<213> ORGANISM: Artificial Sequence
<220> FEATURE:
<223> OTHER INFORMATION: chemically-synthesized oligonucleotide

<400> SEQUENCE: 18
cttctccgtc g    11

<210> SEQ ID NO 19
<211> LENGTH: 51
<212> TYPE: DNA
<213> ORGANISM: Artificial Sequence
<220> FEATURE:
<223> OTHER INFORMATION: chemically-synthesized oligonucleotide
<220> FEATURE:
<221> NAME/KEY: misc_feature
<222> LOCATION: (25)..(28)
<223> OTHER INFORMATION: n is a, c, g, or t

<400> SEQUENCE: 19
aggtcgcatc gcggcgcagc cgtgnnnncg gcgcacgtcg gaagaggcag c    51

<210> SEQ ID NO 20
<211> LENGTH: 51
<212> TYPE: DNA
<213> ORGANISM: Artificial Sequence
<220> FEATURE:
<223> OTHER INFORMATION: chemically-synthesized oligonucleotide
<220> FEATURE:
<221> NAME/KEY: misc_feature
<222> LOCATION: (25)..(28)
<223> OTHER INFORMATION: n is a, c, g, or t

<400> SEQUENCE: 20
tccagcgtag cgccgcgtcg gcacnnnngc cgcgtgcagc cttctccgtc g    51

```
<210> SEQ ID NO 21
<211> LENGTH: 36
<212> TYPE: DNA
<213> ORGANISM: Artificial Sequence
<220> FEATURE:
<223> OTHER INFORMATION: chemically-synthesized oligonucleotide
<220> FEATURE:
<221> NAME/KEY: misc_feature
<222> LOCATION: (25)..(28)
<223> OTHER INFORMATION: n is a, c, g, or t

<400> SEQUENCE: 21
aggtcgcatc gcggcgcagc cgtgnnnncg gcgcac                              36

<210> SEQ ID NO 22
<211> LENGTH: 39
<212> TYPE: DNA
<213> ORGANISM: Artificial Sequence
<220> FEATURE:
<223> OTHER INFORMATION: chemically-synthesized oligonucleotide
<220> FEATURE:
<221> NAME/KEY: misc_feature
<222> LOCATION: (25)..(28)
<223> OTHER INFORMATION: n is a, c, g, or t

<400> SEQUENCE: 22
tccagcgtag cgccgcgtcg gcacnnnngc cgcgtgcag                           39

<210> SEQ ID NO 23
<211> LENGTH: 16
<212> TYPE: DNA
<213> ORGANISM: Artificial Sequence
<220> FEATURE:
<223> OTHER INFORMATION: chemically-synthesized oligonucleotide
<220> FEATURE:
<221> NAME/KEY: misc_feature
<222> LOCATION: (2)..(4)
<223> OTHER INFORMATION: n is a, c, g, or t

<400> SEQUENCE: 23
cnnntgaaga cgcagc                                                    16

<210> SEQ ID NO 24
<211> LENGTH: 12
<212> TYPE: DNA
<213> ORGANISM: Artificial Sequence
<220> FEATURE:
<223> OTHER INFORMATION: chemically-synthesized oligonucleotide

<400> SEQUENCE: 24
acttctgcgt cg                                                        12

<210> SEQ ID NO 25
<211> LENGTH: 16
<212> TYPE: DNA
<213> ORGANISM: Artificial Sequence
<220> FEATURE:
<223> OTHER INFORMATION: chemically-synthesized oligonucleotide
<220> FEATURE:
<221> NAME/KEY: misc_feature
<222> LOCATION: (2)..(4)
<223> OTHER INFORMATION: n is a, c, g, or t

<400> SEQUENCE: 25
gnnnggtctc gcagct                                                    16

<210> SEQ ID NO 26
<211> LENGTH: 12
<212> TYPE: DNA
```

```
<213> ORGANISM: Artificial Sequence
<220> FEATURE:
<223> OTHER INFORMATION: chemically-synthesized oligonucleotide

<400> SEQUENCE: 26
ccagagcgtc ga                                                              12

<210> SEQ ID NO 27
<211> LENGTH: 17
<212> TYPE: DNA
<213> ORGANISM: Artificial Sequence
<220> FEATURE:
<223> OTHER INFORMATION: chemically-synthesized oligonucleotide
<220> FEATURE:
<221> NAME/KEY: misc_feature
<222> LOCATION: (2)..(4)
<223> OTHER INFORMATION: n is a, c, g, or t

<400> SEQUENCE: 27
annntgccac ctgcgca                                                         17

<210> SEQ ID NO 28
<211> LENGTH: 13
<212> TYPE: DNA
<213> ORGANISM: Artificial Sequence
<220> FEATURE:
<223> OTHER INFORMATION: chemically-synthesized oligonucleotide

<400> SEQUENCE: 28
acggtggacg cgt                                                             13

<210> SEQ ID NO 29
<211> LENGTH: 16
<212> TYPE: DNA
<213> ORGANISM: Artificial Sequence
<220> FEATURE:
<223> OTHER INFORMATION: chemically-synthesized oligonucleotide
<220> FEATURE:
<221> NAME/KEY: misc_feature
<222> LOCATION: (2)..(4)
<223> OTHER INFORMATION: n is a, c, g, or t

<400> SEQUENCE: 29
tnnncgtctc gcagct                                                          16

<210> SEQ ID NO 30
<211> LENGTH: 12
<212> TYPE: DNA
<213> ORGANISM: Artificial Sequence
<220> FEATURE:
<223> OTHER INFORMATION: chemically-synthesized oligonucleotide

<400> SEQUENCE: 30
gcagagcgtc ga                                                              12

<210> SEQ ID NO 31
<211> LENGTH: 35
<212> TYPE: DNA
<213> ORGANISM: Artificial Sequence
<220> FEATURE:
<223> OTHER INFORMATION: chemically-synthesized oligonucleotide
<220> FEATURE:
<221> NAME/KEY: misc_feature
<222> LOCATION: (25)..(28)
<223> OTHER INFORMATION: n is a, c, g, or t

<400> SEQUENCE: 31
aggtcgcatc gcggcgcagc cgtgnnnncg gcgca                                     35
```

```
<210> SEQ ID NO 32
<211> LENGTH: 34
<212> TYPE: DNA
<213> ORGANISM: Artificial Sequence
<220> FEATURE:
<223> OTHER INFORMATION: chemically-synthesized oligonucleotide
<220> FEATURE:
<221> NAME/KEY: misc_feature
<222> LOCATION: (25)..(28)
<223> OTHER INFORMATION: n is a, c, g, or t

<400> SEQUENCE: 32
aggtcgcatc gcggcgcagc cgtgnnnncg gcgc                               34

<210> SEQ ID NO 33
<211> LENGTH: 38
<212> TYPE: DNA
<213> ORGANISM: Artificial Sequence
<220> FEATURE:
<223> OTHER INFORMATION: chemically-synthesized oligonucleotide
<220> FEATURE:
<221> NAME/KEY: misc_feature
<222> LOCATION: (25)..(28)
<223> OTHER INFORMATION: n is a, c, g, or t

<400> SEQUENCE: 33
tccagcgtag cgccgcgtcg gcacnnnngc cgcgtgca                           38
```